(12) United States Patent
Deliwala et al.

(10) Patent No.: US 11,674,797 B2
(45) Date of Patent: Jun. 13, 2023

(54) SELF-ALIGNED LIGHT ANGLE SENSOR USING THIN METAL SILICIDE ANODES

(71) Applicant: Analog Devices, Inc., Norwood, MA (US)

(72) Inventors: Shrenik Deliwala, Andover, MA (US); Paul W. Stevens, Norwood, MA (US); William Edward O'Mara, Methuen, MA (US)

(73) Assignee: Analog Devices, Inc., Norwood, MA (US)

( * ) Notice: Subject to any disclaimer, the term of this patent is extended or adjusted under 35 U.S.C. 154(b) by 411 days.

(21) Appl. No.: 16/826,257

(22) Filed: Mar. 22, 2020

(65) Prior Publication Data

US 2021/0293535 A1   Sep. 23, 2021

(51) Int. Cl.
*G01B 11/27* (2006.01)
*H01L 29/66* (2006.01)
*H01L 29/872* (2006.01)

(52) U.S. Cl.
CPC ...... *G01B 11/272* (2013.01); *H01L 29/66143* (2013.01); *H01L 29/872* (2013.01)

(58) Field of Classification Search
CPC ............ G01B 11/272; H01L 29/66143; H01L 29/872
See application file for complete search history.

(56) References Cited

U.S. PATENT DOCUMENTS

| | | | |
|---|---|---|---|
| 4,254,428 A | * | 3/1981 | Feth ........................ H01L 21/74 438/581 |
| 4,441,810 A | | 4/1984 | Momose et al. |
| 4,688,933 A | | 8/1987 | Lapeyre |
| 4,956,546 A | | 9/1990 | Nishibe et al. |
| 5,187,540 A | | 2/1993 | Morrison |
| 5,196,689 A | | 3/1993 | Sugita et al. |

(Continued)

FOREIGN PATENT DOCUMENTS

| | | |
|---|---|---|
| CN | 1989895 A | 7/2007 |
| DE | 10046785 | 4/2002 |

(Continued)

OTHER PUBLICATIONS

OAI mailed in DE Patent Application Serial No. 112012005324.9 dated Apr. 10, 2017, 18 pages [EN summary included].

(Continued)

*Primary Examiner* — Shahed Ahmed
*Assistant Examiner* — Vicki B. Booker
(74) *Attorney, Agent, or Firm* — ArentFox Schiff

(57) ABSTRACT

Aspects of the embodiments are directed to non-contact systems, methods and devices for optical detection of objects in space at precise angles. This method involves the design and fabrication of photodiode arrays for measuring angular response using self-aligned Schottky platinum silicide (PtSi) PIN photodiodes (PN-diodes with an intrinsic layer sandwiched in between) that provide linear angular measurements from incident light in multiple dimensions. A self-aligned device is defined as one in which is not sensitive to photomask layer registrations. This design eliminates device offset between "left" and "right" channels for normal incident light as compared to more conventional PIN diode constructions.

16 Claims, 18 Drawing Sheets

(56) References Cited

U.S. PATENT DOCUMENTS

| | | | |
|---|---|---|---|
| 5,305,091 A | 4/1994 | Gelbart et al. |
| 5,361,117 A | 11/1994 | Nonaka |
| 5,367,373 A | 11/1994 | Busch-Vishniac et al. |
| 5,422,693 A | 6/1995 | Vogeley et al. |
| 5,527,822 A | 6/1996 | Scheiner |
| 5,574,479 A | 11/1996 | Odell |
| 5,598,187 A | 1/1997 | Ide et al. |
| 5,602,384 A | 2/1997 | Nunogaki et al. |
| 5,627,565 A | 5/1997 | Morishita et al. |
| 5,644,126 A | 7/1997 | Ogawa |
| 5,644,385 A | 7/1997 | Mizuno |
| 5,793,353 A | 8/1998 | Wu |
| 5,796,387 A | 8/1998 | Curran et al. |
| 5,825,481 A | 10/1998 | Alofs et al. |
| 5,892,501 A | 4/1999 | Kim et al. |
| 5,900,863 A | 5/1999 | Numazaki |
| 5,909,296 A | 6/1999 | Tsacoyeanes |
| 5,974,365 A | 10/1999 | Mitchell |
| 6,014,129 A | 1/2000 | Umeda et al. |
| 6,026,313 A | 2/2000 | Kexin |
| 6,130,663 A | 10/2000 | Null |
| 6,181,877 B1 | 1/2001 | Yoshida |
| 6,280,327 B1 | 8/2001 | Leifer et al. |
| 6,330,064 B1 | 12/2001 | Rieder |
| 6,343,171 B1 | 1/2002 | Yoshimura et al. |
| 6,473,189 B1 | 10/2002 | Reedy |
| 6,495,833 B1 | 12/2002 | Alfano et al. |
| 6,498,860 B1 | 12/2002 | Sasaki et al. |
| 6,522,395 B1 | 2/2003 | Bamji et al. |
| 6,529,281 B2 | 3/2003 | Takeshita et al. |
| 6,567,071 B1 | 5/2003 | Curran et al. |
| 6,597,443 B2 | 7/2003 | Boman |
| 6,997,879 B1 | 2/2006 | Turcott |
| 7,012,691 B2 | 3/2006 | Sugiyama et al. |
| 7,158,659 B2 | 1/2007 | Baharav et al. |
| 7,352,477 B2 | 4/2008 | Seo |
| 7,461,543 B2 | 12/2008 | Degertekin |
| 7,473,884 B2 | 1/2009 | Fouquet et al. |
| 7,505,033 B2 | 3/2009 | Guo et al. |
| 7,655,937 B2 | 2/2010 | Hotelling et al. |
| 7,737,409 B2 | 6/2010 | Deliwala et al. |
| 7,787,122 B2 | 8/2010 | Saito et al. |
| 7,852,317 B2 | 12/2010 | Grunnet-Jepsen et al. |
| 7,931,535 B2 | 4/2011 | Ikeda et al. |
| 7,944,551 B2 | 5/2011 | Addison et al. |
| 7,978,311 B2 | 7/2011 | Deliwala |
| 8,310,656 B2 | 11/2012 | Zalewski |
| 2001/0043337 A1 | 11/2001 | Takeshita et al. |
| 2002/0053635 A1 | 5/2002 | Schroter et al. |
| 2003/0090650 A1 | 5/2003 | Fujieda |
| 2003/0197114 A1 | 10/2003 | Muesch |
| 2003/0223085 A1 | 12/2003 | Rekimoto |
| 2004/0135825 A1 | 7/2004 | Brosnan |
| 2004/0222969 A1 | 11/2004 | Buchenrieder |
| 2004/0225207 A1 | 11/2004 | Bae et al. |
| 2004/0266528 A1 | 12/2004 | Wang |
| 2005/0259097 A1 | 11/2005 | Lehoty et al. |
| 2006/0221250 A1 | 10/2006 | Rossbach et al. |
| 2007/0018970 A1 | 1/2007 | Tabasso et al. |
| 2007/0078311 A1 | 4/2007 | Al-Ali et al. |
| 2007/0103698 A1 | 5/2007 | Liu et al. |
| 2007/0138377 A1 | 6/2007 | Zarem |
| 2007/0165225 A1 | 7/2007 | Trainer |
| 2007/0252821 A1 | 11/2007 | Hollemans et al. |
| 2007/0265075 A1 | 11/2007 | Zalewski |
| 2008/0009690 A1 | 1/2008 | Debreczeny et al. |
| 2008/0013826 A1 | 1/2008 | Hillis et al. |
| 2008/0075474 A1 | 3/2008 | Kawai |
| 2008/0089587 A1 | 4/2008 | Kim et al. |
| 2008/0100825 A1 | 5/2008 | Zalewski |
| 2008/0150898 A1 | 6/2008 | Low et al. |
| 2008/0215974 A1 | 9/2008 | Harrison et al. |
| 2008/0220814 A1 | 9/2008 | Hedtke et al. |
| 2008/0221418 A1 | 9/2008 | Al-Ali et al. |
| 2008/0278445 A1 | 11/2008 | Sweetser et al. |
| 2009/0062667 A1 | 3/2009 | Fayram et al. |
| 2009/0078858 A1 | 3/2009 | Fouquet et al. |
| 2009/0085869 A1 | 4/2009 | Destura et al. |
| 2009/0091532 A1 | 4/2009 | Hockett |
| 2009/0092284 A1 | 4/2009 | Breed et al. |
| 2009/0280843 A1 | 11/2009 | Wisebourt et al. |
| 2009/0325408 A1 | 12/2009 | Wong et al. |
| 2010/0201812 A1 | 8/2010 | McGibney et al. |
| 2010/0023151 A1 | 9/2010 | Deliwala |
| 2010/0271617 A1 | 10/2010 | Darnink et al. |
| 2010/0277431 A1 | 11/2010 | Klinghult |
| 2010/0309457 A1 | 12/2010 | Cui et al. |
| 2011/0043623 A1* | 2/2011 | Fukuta ............... G02B 27/0018 348/222.1 |
| 2012/0105823 A1 | 5/2012 | Hardegger et al. |
| 2012/0280107 A1 | 11/2012 | Skurnik et al. |
| 2014/0375985 A1 | 12/2014 | Deliwala |

FOREIGN PATENT DOCUMENTS

| | | |
|---|---|---|
| DE | 10218160 | 4/2002 |
| DE | 69323618 | 2/2005 |
| DE | 102009046740 | 7/2011 |
| EP | 0271340 A1 | 6/1988 |
| EP | 0625692 | 5/1994 |
| EP | 0905646 A1 | 3/1999 |
| WO | 00/07148 | 2/2000 |
| WO | 2011/058190 | 5/2011 |

OTHER PUBLICATIONS

PCT International Search Report and Written Opinion issued in PCT/US2010/036438, dated Jul. 27, 2010, 9 pages.

PCT International Search Report and Written Opinion issued in PCT/US2009/041539, dated Aug. 5, 2009, 12 pages.

PCT International Search Report and Written Opinion issued in PCT/US2010/035604, dated Jul. 26, 2010, 11 pages.

Supplementary EP Search Report issued in EP Application No. 10781228, dated Jul. 31, 2014, 9 pages.

Amann, Markus-Christian, Thierry Bosch, Marc Lescrure, Risto Myllyla, Marc Rioux, "Laser ranging: a critical review of usual techniques for distance measurement", Optical Engineering, vol. 40, No. 1, Jan. 2001, pp. 10-19.

PCT International Search Report and Written Opinion for PCT/US2012/066969 dated Feb. 6, 2013.

EP Communication including Supplementary European Search Report issued in EP Appln. No. 10781029.3, dated Jun. 27, 2014, 6 pages.

Tsaur et al., *PtSi Schottky-Barrier Focal Plane Arrays for Multispectral Imaging in Ultraviolet, Visible, and Infrared Spectral Bands*, IEEE Electron Device Letters, vol. 11, No. 4, Apr. 1990, 3 pages.

Extended European Search Report in EP 21158280.4 dated Aug. 13, 2021, 7 pages.

\* cited by examiner

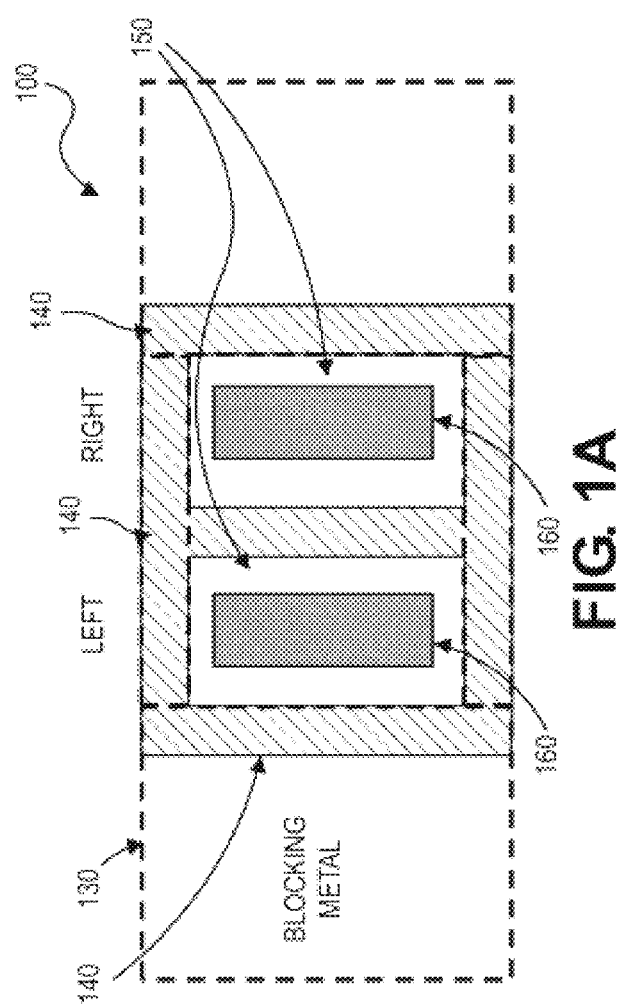

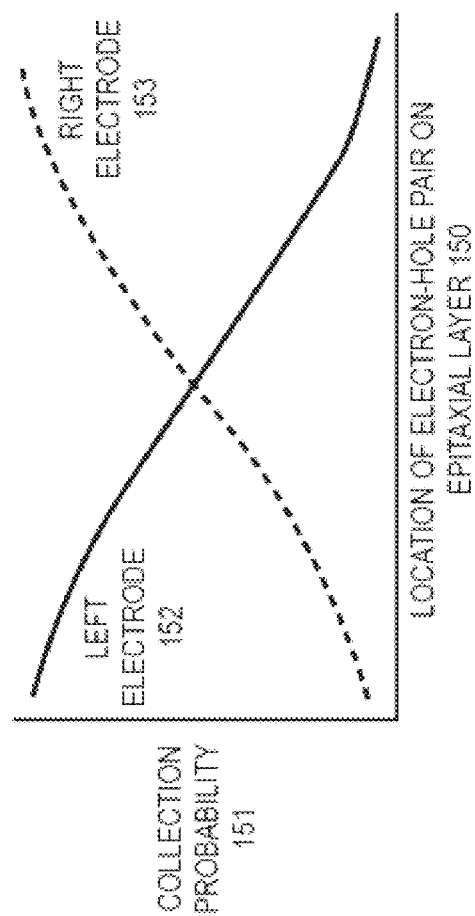

SELF-ALIGNED LIGHT ANGLE SENSOR USING THIN METAL SILICIDE ANODES

CROSS-REFERENCE TO RELATED APPLICATIONS

This application is related to U.S. Utility patent application Ser. No. 13/924,797 entitled, "OPTICAL ANGLE MEASUREMENT" filed on Jun. 24, 2013, currently granted U.S. Pat. No. 9,435,641, and to U.S. Utility patent application Ser. No. 13/329,510 entitled, "LENS-LESS OPTICAL POSITION MEASURING SENSOR" filed on Dec. 19, 2011, currently granted U.S. Pat. No. 9,702,690, both of which are hereby incorporated by reference in their entirety.

FIELD OF THE DISCLOSURE

The present disclosure relates to a self-aligned light angle sensor. More specifically, this disclosure describes apparatus and methods relating to fabricating self-aligned light angle sensors using thin metal silicide anodes and applications thereto.

BACKGROUND

Light angle sensors are used in a variety of applications, for example, gesture for user interface control in portable devices, object location tracking, industrial and automation monitoring, angle sensing, proximity sensing and object distance measurement (triangulation). Systems using angle sensors may need to be calibrated for zero angle of incident light. This can become a timely and costly matter.

Optical sensing technology has been used to locate and track movement of objects in multiple dimensions. Traditional optical position sensitive detectors use optical lenses to focus incident light on a particular area of the detector to determine an angular location of an object emitting or reflecting the light. The lenses focus and map light rays emitting from the object to a particular location on the surface of the sensor. The angular location of the object emitting the light may be calculated from the mapped location of the light rays at the sensor and the properties of the lens. While lenses were needed to focus the light on a particular area of the detector in order to measure the properties of the light emitted from a light source, the use of lenses in these detectors has several limitations.

First, optical lenses are required to be positioned at a height at least equal to the focal length of the lens above the light detecting surface. This required separation between the lens and the light detecting surface consumes extra space in electronic devices, which makes it difficult to reduce the size of the device. Second, the lenses also represent a cost component of a detector. Eliminating the lens from these detectors would therefore reduce the height of the detectors and make them less costly to manufacture.

Existing lens-less detector solutions used two or more photodetectors isolated from each other by a trench between them. The trench was aligned with an aperture so that the quantity of incident light reaching each of the photodetectors after passing through the aperture would change as the angle of the incident light on the aperture changed. However, the trench reduced the light collection efficiency of these photodetectors because the light passing through the aperture that reaches the trench would not be detected by the photodetectors.

In micromechanical devices, the trench may be several microns wide and may reduce the light collection efficiency of the photodetectors by 10% to 50% depending on the slit width. Additionally, trenches have been difficult to manufacture on germanium based epitaxial layers, which provide improved light detection capabilities over silicon based epitaxial layers.

Accordingly, there is a need for trenchless optical detectors generating an output used to calculate angular information about a light source. The inventors of the present disclosure have identified these shortcomings and recognized a need for a new alignment sensor is self-aligning and doesn't require difficult registration and/or calibration.

This disclosure is intended to provide an overview of subject matter of the present patent application. It is not intended to provide an exclusive or exhaustive explanation of the invention. Further limitations and disadvantages of conventional and traditional approaches will become apparent to one of skill in the art, through comparison of such systems with some aspects of the present invention as set forth in the remainder of the present application with reference to the drawings.

SUMMARY OF THE DISCLOSURE

Aspects of the embodiments are directed to non-contact systems, methods and devices for optical detection of objects in space at precise angles. This method involves the design and fabrication of photodiode arrays for measuring angular response using self-aligned Schottky platinum silicide (PtSi) PIN photodiodes (PN-diodes with an intrinsic layer sandwiched in between) that provide linear angular measurements from incident light in multiple dimensions. A self-aligned device is defined as one in which is not sensitive to photomask layer registrations. This design eliminates device offset between "left" and "right" channels for normal incident light as compared to more conventional PIN diode constructions.

According to one aspect of the present disclosure is an apparatus of optical detection comprising a substrate, an intrinsic layer, a metal silicide anode diode (Schottky Diode) and a metal light block arranged in an array comprising of left and right pairs of photodiodes.

According to another aspect of the present disclosure is an apparatus wherein each side connected in parallel with an optical filter coating layer applied over the top of the structure.

According to another aspect of the present disclosure is an apparatus wherein the device is self-aligned such that the zero (normal) angle is guaranteed by design (no offset error).

According to another aspect of the present disclosure is an apparatus wherein there are not multiple reflections between the shadow metal and the optical collection layer.

According to another aspect of the present disclosure is an apparatus wherein the ultra-thin shadow metal is configured to avoid reflections from the thick edges of the metal.

According to another aspect of the present disclosure is an apparatus wherein the Ideal Fresnel equation-based operation applies for the angle sensor.

According to another aspect of the present disclosure is an apparatus wherein the device can be tuned for different wavelengths.

According to another aspect of the present disclosure is an apparatus wherein manufacturing is a simplified process flow as compared to traditional designs.

According to one aspect of the present disclosure is an apparatus for a self-aligned light angle sensor which forgoes the need for calibration comprising a substrate, a cathode disposed on the substrate, an intrinsic layer disposed on the cathode.

According to another aspect of the present disclosure, left and right channels are configured to comprise a left and right anode, each of which is disposed on the intrinsic layer and configured to sense light therein.

The first and second aspects further comprises a passivation layer at least partially covering the left and right anode and a blocking member disposed proximally to the left and right anode.

According to one or more aspects of the present disclosure, the left and right anodes comprise metal.

According to another aspect of the present disclosure, the left and right anodes comprise a metal silicide.

According to another aspect of the present disclosure, the metal silicide is configured as a Schottky diode.

According to one or more aspects of the present disclosure, the blocking member comprises metal.

According to another aspect of the present disclosure, the intrinsic layer comprises undoped silicon.

According to another aspect of the present disclosure, the self-aligned light angle sensor further comprises a dielectric layer disposed over blocking member.

According to another aspect of the present disclosure, the self-aligned light angle sensor further comprises an optical filter.

According to another aspect of the present disclosure, the substrate is configured to be the cathode.

According to one or more aspects of the present disclosure, a method for fabricating a self-aligned light angle sensor comprises providing a substrate, depositing a cathode on the substrate, epitaxially growing an intrinsic layer on the cathode, providing a left and right anode, each of which is disposed on the intrinsic layer and configured to sense light therein.

According to another aspect of the present disclosure, the method further comprises depositing a passivation layer at least partially covering the left and right anode and disposing a blocking member proximally to the left and right anode.

According to another aspect of the present disclosure, the left and right anodes comprise a metal silicide.

According to another aspect of the present disclosure, the method further comprises configuring the metal silicide to function as a Schottky diode.

According to another aspect of the present disclosure, the blocking member comprises a very thin layer of metal.

According to another aspect of the present disclosure, the intrinsic layer comprises undoped silicon.

According to another aspect of the present disclosure, the method further comprises depositing an optical filter.

According to another aspect of the present disclosure, the method further comprises measuring a first current on the left anode and a second current on the right anode.

According to another aspect of the present disclosure, the method further comprises calculating a ratio of the first and second currents.

According to another aspect of the present disclosure, the method further comprises deriving an angle of incidence based on the ratio of the first and second currents.

According to one or more aspects of the present disclosure, an apparatus comprises a means for providing a substrate, means for depositing a cathode on the substrate, a means for epitaxially growing an intrinsic layer on the cathode, a means for providing a left and right anode, each of which is disposed on the intrinsic layer and configured to sense light therein, a means for depositing a passivation layer at least partially covering the left and right anode, and a means for disposing a blocking member proximally to the left and right anode.

According to another aspect of the present disclosure, the apparatus further comprises an analog front end configured to derive an angle of incidence based on a ratio of the first and second currents measure from the left and right anodes, respectively.

The drawings show exemplary stable, robust method for measuring sensors in a manifold of applications and configurations thereof. Variations of these circuits, for example, changing the positions of, adding, or removing certain elements from the circuits are not beyond the scope of the present invention. The illustrated stable measurement circuit devices and configurations are intended to be complementary to the support found in the detailed description.

BRIEF DESCRIPTION OF THE DRAWINGS

The present disclosure is best understood from the following detailed description when read with the accompanying figures. It is emphasized that, in accordance with the standard practice in the industry, various features are not necessarily drawn to scale, and are used for illustration purposes only. Where a scale is shown, explicitly or implicitly, it provides only one illustrative example. In other embodiments, the dimensions of the various features may be arbitrarily increased or reduced for clarity of discussion.

For a fuller understanding of the nature and advantages of the present invention, reference is made to the following detailed description of preferred embodiments and in connection with the accompanying drawings, in which:

FIG. 1A shows an exemplary top-down view of a light angle sensor, in accordance with one or more embodiments of the disclosure provided herein;

FIG. 1C demonstrates an exemplary graph of collection probability as a function of the location with respect to the light angle sensor in FIG. 1B, in accordance with some embodiments of the disclosure provided herein;

DETAILED DESCRIPTION

Figure 1B:
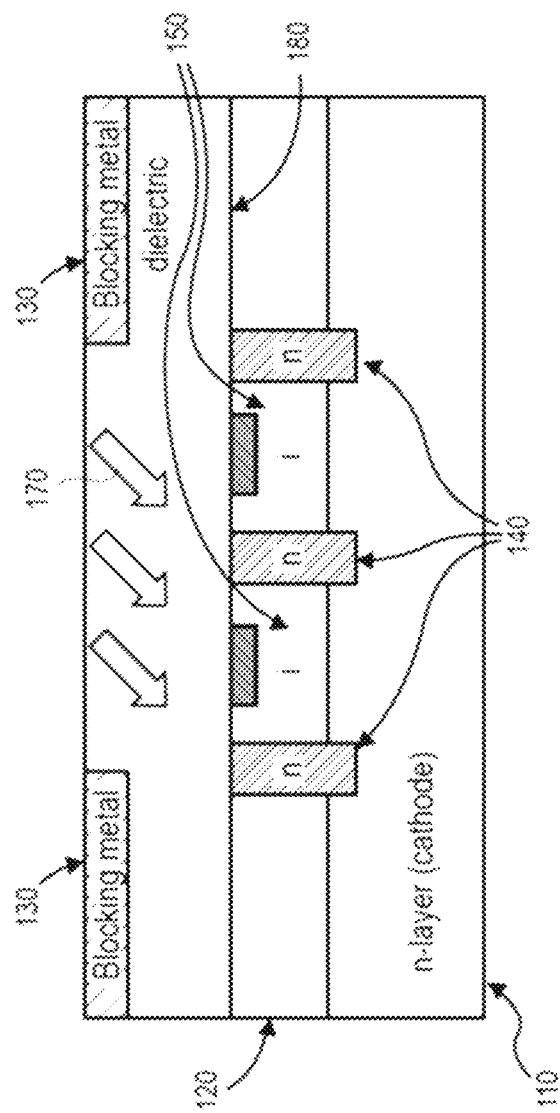
FIG. 1B shows an exemplary sideview of a light angle sensor, in accordance with one or more embodiments of the disclosure provided herein.

The present disclosure relates to a self-aligned light angle sensor. More specifically, this disclosure describes apparatus and methods relating to fabricating self-aligned light angle sensors using thin metal silicide anodes and applications thereto.

The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Other objects, advantages and novel features of the disclosure are set forth in the proceeding in view of the drawings where applicable.

In the present state of the art, light angle sensors typically require a high degree of precision of the aperture during manufacturing (packaging). This requires several layers of registration with the added complexity of registration marks. Alternatively, aperture alignment can have a higher tolerance, however, this requires calibration, typically at the factory. During calibration, orthogonal light is incident on the light angle sensor. A ratio between the left and right channels is measured. This ratio is compensated for in operation. Both have several drawbacks, in that they require additional complexity, parts and/or labor for both the fabricator and end user.

In different embodiments, an epitaxial layer may be provided on a surface of a substrate. The epitaxial layer may be covered by a periphery surface of the optical detector. The periphery surface may include an aperture for incident light to pass through and reach the epitaxial layer. Two or more electrodes may be arranged at different positions in the epitaxial layer from the aperture so that the electron-hole pairs generated in the epitaxial layer from the incident light passing through the aperture and reaching the epitaxial layer have a varying probability of being collected by each of the electrodes as the angle of the incident light changes.

The electrodes may be arranged at different depths in the epitaxial layer. In some instances, the electrodes may only partially penetrate a surface of epitaxial layer opposite that contacting the substrate. In other instances, one or more of the electrodes may be positioned further into the epitaxial layer and wholly contained on all sides by the epitaxial layer.

The specific probability for each electrode may depend on the location of the electrode as compared to the location of the other electrodes and the location of the generated electron-hole pair in the epitaxial layer caused by the portion of the incident light reaching the epitaxial layer. The specific probability may also depend on a bias voltage applied to the substrate, the resistivity of the epitaxial layer, the thickness of the epitaxial layer, the distance between the aperture and the epitaxial layer, and the type and thickness of a filler, if any, between the periphery and the epitaxial layer.

The epitaxial layer may be continuous and have a continuous aperture-facing surface between each of the electrodes associated with a particular aperture. The epitaxial layer surface may be continuous when it does not contain trenches or other electrical isolators that impede the absorption of the incident light in the epitaxial layer resulting in the generation of electron-hole pairs in the epitaxial layer.

As result of not including the isolators, light passing through the aperture is absorbable and subsequently detectable at any and all parts of the continuous surface of the epitaxial layer encompassing the electrodes associated with that aperture. This results in improved light detection capabilities by the electrodes inserted in the epitaxial layer, as the continuous surface eliminates any dead zones in the epitaxial layer associated with the trenches in the prior art.

Additionally, the continuous surface of the epitaxial layer enables smaller sized apertures that provide higher angular resolution of the angle of the incident light. Smaller sized apertures are enabled because although the smaller apertures allow less light to reach the epitaxial layer, less light is needed due to the improved light detection capabilities of continuous surface epitaxial layer.

The light detection capabilities of these optical detectors with continuous surface epitaxial layers may be further improved by including one or more lenses or replacing the aperture with a lens. If the light absorption depth of the epitaxial layer is shallow for a wavelength of the incident light, then the lens may be configured to focus the incident light at or near the surface of the epitaxial layer. However, if the wavelength of the incident light has a deeper absorption depth then the lens may be configured to focus the incident light at a different depth in the epitaxial layer.

Continuous surface epitaxial layers may also be easier to manufacture than epitaxial layers with trenches or other isolators subdividing the layer. Certain types of epitaxial layers, such as germanium-based layers, including but not limited to germanium or germanium-silicon layers, may be easily created to have a continuous surface. It may be commercially impractical based on cost or resource limitations to subdivide these types of epitaxial layers into electrically isolated regions using trenches or other isolators. Additionally, any trenches used to isolate photodetectors also reduce the surface area of epitaxial layer available to absorb and detect incident light. This reduced surface area reduces the detection efficiency of the optical detector for a photodetector of a particular size.

In one or more embodiments of the disclosure, the aperture may be defined by electrodes and/or blocking members disposed in close proximity to the epitaxial layers. In some embodiments, an optical detector may include an integrated circuit having an aperture in a surface of the integrated circuit and at least two electrically isolated photodetectors, which may be aligned with respect to the aperture so that a quantity of the incident light from a light source detected at each of the photodetectors changes as an angle of the incident light changes with respect to the aperture.

In some instances, the aperture and photodetectors may be monolithically manufactured into or on top of a single chip of silicon or other semiconductor to form the integrated circuit. In other instances, the aperture and photodetectors need not be part of an integrated circuit. In some instances, the optical detector may also include a measuring arrangement to quantify the angle of the incident light from a light source detected at the photodetectors after passing through the aperture.

The aperture may be included in a first surface of an integrated circuit forming the optical detector. The photodetectors may be embedded in the integrated circuit below the first surface. In some instances, the aperture may be monolithically constructed with the detectors to ensure precise alignment of the aperture and the photodetectors. Improving the precision of the alignment between the aperture and the photodetectors may improve the accuracy of the measured angular position of the light source. The detector has no need for an external lens.

In some instances, the surface of the integrated circuit having the aperture may be made from a metal or an opaque thin-film material. In these instances, a slit, opening, hole, or other absence of the metal or material may be provided to create the aperture. The aperture may be positioned between a light source and the photodetectors to allow light to pass through the aperture and reach the photodetectors.

The photodetectors may be electrically isolated from each other, positioned next to each other in a side-by-side configuration, and then aligned with the aperture so that a proportion of the light detected at the photodetectors changes as an angle of light incident to the aperture changes. There are many techniques for electrically isolating photodetectors positioned extremely close to each other. These techniques include using trenches, such as partial etchings and full isolation trenches, or junction isolation methods to electrically isolate the photodetectors from each other, though in other embodiments other insulators or techniques may be used.

The photodetectors may include PIN junction photodiodes having a lightly doped near intrinsic semiconductor region between the p-type and n-type semiconductor regions. The PIN junction photodiodes may be constructed so that an internal electric field due to bias as well as built-in potential forces cause essentially vertical motion of the photo-generated carriers. This may be accomplished with a high-resistivity epitaxial growth of silicon forming the PIN junction.

The measuring arrangement may include circuitry enabling the use of photocurrents to quantify the light detected at the photodetectors. Alternatively, the measuring arrangement may include circuitry enabling photodetector-initiated changes to a resistance or conductivity parameter of a circuit to quantify the light detected at the photodetectors. Other techniques for quantifying the light detected at the photodetectors may also be used.

The surface of the integrated circuit may include an aperture in the shape of a slit, round hole, square hole, or other shape, such as a polygon, oval, or freeform shape.

The size and shape of the aperture and photodetectors may be selected to provide for varying shadows on each of the photodetectors as an angle of light originating from a light source incident to the aperture changes. The measuring arrangement may include circuitry to calculate this angle of light incident to the aperture from the quantified amount of light detected at the photodetectors.

In some instances where the surface of the integrated circuit containing the aperture is a metallic or other reflective medium, the edges of the aperture may be beveled to minimize reflections at an aperture edge that may erroneously cause the light to be reflected off the aperture edge and onto an incorrect light detecting surface of a photodetector. In some instances, the beveled aperture edge may be directed away from the photodetector to cause the light striking the beveled edge to be reflected away from the photodetectors, though in other instances, the beveled aperture edge may be directed in another direction.

FIG. 1A shows an exemplary top-down view of a light angle sensor 100, in accordance with one or more embodiments of the disclosure provided herein. Light angle sensor 100 comprises blocking metal 130, n-doped frame 140, p-type anodes 160, and intrinsic bulk 150. Left and right channels are bifurcated within the bulk, the operation of which will be discussed in greater detail later in the disclosure.

In one or more embodiments, blocking metal comprises any optically opaque material. As would be understood by anyone skilled in the art, optically opaque doesn't necessarily mean the visible spectrum. As will be described later, light of longer wavelengths is frequently used. For example, near infrared (NIR) and midwave infrared (MWIR) can be used in light angle sensor 100. However, other wavelengths are not beyond the scope of the present disclosure.

In a preferred embodiment, blocking material is generally: conductive, substantially reflective, and/or substantially lossy beyond the penetration depth. That is, the material would have an imaginary part its complex impedance so as to largely prevent electromagnetic waves from passing therethrough, evanescent or otherwise.

In one or more embodiments, epitaxial bulk 150 comprising one or more epitaxially layers of intrinsic silicon. However, other epitaxial layer materials are not beyond the scope of the present invention. Epitaxy refers to a type of crystal growth or material deposition in which new crystalline layers are formed with a well-defined orientation with respect to the crystalline substrate. The new layers formed are called the epitaxial film or epitaxial layer.

The relative orientation of the epitaxial layer to the crystalline substrate is defined in terms of the orientation of the crystal lattice of each material. For epitaxial growth, the new layer will be crystalline and will all have a single orientation relative to the substrate; amorphous growth or multicrystalline growth with random crystal orientation does not meet this criterion.

In some embodiments, n-type frame 140 is a doped n-type semiconductor having an n-type group III material, such as, n-type GaN. However, other semiconductor materials are not beyond the scope of the present invention. N-type frame 140 can be made by adding an impurity to a pure semiconductor such as silicon or germanium. The impurities used may be phosphorus, arsenic, antimony, bismuth or some other chemical element. As is known in the art, these are called donor impurities. The impurity is called a donor because it gives a free electron to a semiconductor. The purpose of doing this is to make more charge carriers, or electron wires available in the material for conduction. The final material is a lot more conductive than the original silicon or germanium.

In one or more embodiments, p-type electrodes 160 comprise p-type semiconductors. One or more trivalent impurities is added to an intrinsic or pure semiconductor (silicon or germanium), then it is said to be an p-type semiconductor. Trivalent impurities such as Boron (B), Gallium (Ga), Indium (In), Aluminum (Al) etc. are called acceptor impurity. Ordinary semiconductors are made of materials that do not conduct (or carry) an electric current very well but are not highly resistant to doing so. They fall half way between conductors and insulators. An electric current occurs when electrons move through a material. In order to move, there must be an electron 'hole' in the material for the electron to move into. A p-type semiconductor has more holes than electrons. This allows the current to flow along the material from hole to hole but only in one direction.

Semiconductors are most often made from silicon. Silicon is an element with four electrons in its outer shell. To make a p-type semiconductor, extra materials like boron or aluminum are added to the silicon. These materials have only three electrons in their outer shell. When the extra material replaces some of the silicon it leaves a 'hole' where the fourth electron would have been if the semiconductor was pure silicon.

FIG. 1B shows an exemplary sideview of a light angle sensor 200, in accordance with one or more embodiments of the disclosure provided herein. Light angle sensor 100 comprises blocking metal 130, n-doped frame 140, p-type anodes 160, and intrinsic bulk 150, and n-layer substrate 110. In some embodiments, n-layer substrate comprised n-type doped silicon and acts as a cathode which will be appreciated by those skilled in the art.

In practice, the p-type anodes 160, the intrinsic bulk 150, and n-type frame 140 are configured as a PIN diode which is used to collect light 170. A PIN diode is a diode with a wide, undoped intrinsic semiconductor region between a p-type semiconductor and an n-type semiconductor region. The p-type and n-type regions are typically heavily doped because they are used for ohmic contacts. The wide intrinsic region is in contrast to an ordinary p-n diode. The wide intrinsic region makes the PIN diode an inferior rectifier (one typical function of a diode), but it makes it suitable for attenuators, fast switches, photodetectors, and high voltage power electronics applications.

Functioning as an optical detector, light angle sensor 100 may include a periphery such as an exterior surface or housing. In those instances where the light angle sensor 100 is formed from a semiconductor, the periphery may be an outer surface of the semiconductor. In those instances where the light angle sensor 100 is formed as an integrated circuit, the periphery may be an exterior surface of the integrated circuit. The periphery may be metallic or made from another substance impervious to light. In some instances, the periphery may be embedded in or part of a dielectric material such as glass or other material commonly used in semiconductor manufacturing.

The periphery may have an aperture that allows incident light 170 to pass through the aperture, not shown. The aperture may be any type of opening in or section of the periphery that is transparent. In some instances, the aperture may be a physical opening or hole in the periphery. In other instances, the aperture may be section of the periphery that is altered to make it transparent or permeable to light without necessarily creating a physical opening or hole. Such an altering may occur in some instances by removing an opaque coating covering a section of the periphery to make it transparent, replacing a section of the periphery with a transparent material, or by other techniques. The aperture may be a slit or pinhole, or it may have any other shape or form.

One or more edges of aperture may be beveled. In some instance, each edge of the aperture directed away from the epitaxial layer may be beveled to reduce an amount of incident light that is reflected off the edge and redirected onto the epitaxial layer. In the present embodiment, blocking elements 130 serve as the aperture for the purpose of the discussion An interior of the light angle sensor 100 may include a n-layer substrate 110 having an epitaxial layer. The epitaxial layer may be applied on a surface of the substrate 110 facing the aperture 110. The epitaxial layer may, in some instances, be a germanium based, silicon based, or germanium and silicon based epitaxial layer. Other types of epitaxial layers may be used in other embodiments. In the present embodiment, intrinsic bulk 150 is grown epitaxially onto the substrate 110.

Two or more p-type electrodes 160 may be situated at least partially in or on the intrinsic bulk 150 so as to electrically contact the intrinsic bulk 150. The contacting of the p-type electrodes 160 to the intrinsic bulk 150 may enable p-type electrodes 160 to collect electron-hole pairs in the intrinsic bulk 150 generated from the absorption of the incident light 120 in the intrinsic bulk 150 to detect a quantity of the light received at the intrinsic bulk 150. The depths that the p-type electrodes 160 are positioned in the intrinsic bulk 150 may be selected to correspond to an expected penetration depth of a wavelength of the incident light 170 to be detected to maximize the collection of electron-hole pairs by the electrode at that penetration depth.

The p-type electrodes 160 may have any shape. For example, in some instances the electrodes may be discrete, point shaped electrodes. In other instances, the electrodes may be continuous electrodes having a length or other dimension corresponding to that of the aperture, such a length corresponding to a slit length of a slit aperture or a rectangular shape corresponding to a rectangularly shaped slit aperture.

The two or more p-type electrodes 160 may be located at predetermined positions relative to the aperture (space between blocking elements 130). For example, in some instances, such as that shown in FIG. 1B, the p-type electrodes 160 may be located at equal distances from a center of the aperture. In other instances, one or more of the p-type electrodes 160 may be located at different distances than other p-type electrodes 160 from the center of the aperture. P-type electrodes 160 may also be located opposite from each other relative to the center of the aperture in some instances, but in other instances, the p-type electrodes 160 may be positioned in different orientations.

The intrinsic bulk 150 may also be continuous and have a continuous surface between each of the electrodes. This continuity ensures that the entire section of the epitaxial layer located between the p-type electrodes 160 is available to absorb light and generate electron-hole pairs. In the past, the presence of trenches and other isolators compartmentalizing the intrinsic bulk 150 prevented maximum absorption of incident light reaching the intrinsic bulk 150 and generation of electron-hole pairs collected by the electrodes.

In general, photodiodes may be formed from the p-type electrodes 160 and substrate 110. If the substrate 110 is an n-type semiconductor then the substrate 110 may function as a common cathode contact while the two p-type electrodes 160 may function as anodes forming p-type electrodes. In some instances, the reverse may occur—the substrate 110 may be a p-type semiconductor anode and the p-type electrodes 160 may be n-type cathodes. In some instances, the light detection ability of the photodiode may be improved by decreasing the doping of the intrinsic bulk 150 or making the intrinsic bulk 150 similar to and/or of the same type as the common electrode substrate 110. This may ensure that the depletion layer surrounds the p-type electrodes 160, effectively isolating the two electrodes from each other. The electrodes would be isolated from each other because the resistance $R_{eff}$ between the two p-type electrodes 160 will be very large in the order of hundreds of mega ohms. The photodiodes may also be biased to measure the incident light in either photoconductive mode or photovoltaic mode.

In the photoconductive mode, the p-type electrodes 160 may be electrically coupled to one or more current sensing devices that is able to identify a relative amount of collected electron-hole pairs at each electrode that were generated in the intrinsic bulk 150 by the absorption of the incident light 170 in the intrinsic bulk 150.

FIG. 1C demonstrates an exemplary graph of collection probability as a function of the location with respect to the light angle sensor in FIG. 1B, in accordance with some embodiments of the disclosure provided herein. FIG. 1C depicts a probability distribution function of a probability 151 that electron-hole pairs generated at different locations in the intrinsic bulk 150 along the axis 150 will be collected by either the electrode on the left side 152 of FIG. 1C (as indicated by the solid plot line) or the electrode on the right side 153 of FIG. 1C (as indicated by the dashed plot line).

Based on this known probability distribution, the measured currents at the respective left 152 and right 153 p-type electrodes 160 ($i_L$ and $i_R$) may be compared to calculate an expected centroid of the incident light 170 between the p-type electrodes 160. An angle of the incident light 170 may then be calculated based on the expected centroid. The probably distribution function may be determined experimentally. This approach of using the probability distribution function to calculate the angle of the incident light 170 may be accurate over only small separation distances between the p-type electrodes 160 on the order of tens of microns rather than the several millimeters needed to build a traditional angle measuring photodiode detector. In instances where a millimeter scale photodetector is needed, several optical detectors may be coupled together to achieve the millimeter scale.

An angle of the incident light 170 passing through the aperture 111 and reaching the intrinsic bulk 150 may be calculated from the current measured at each of the p-type electrodes 160. In the case of two p-type electrodes 160 as shown in FIG. 1B, the angle θ of the incident light 170 may be calculated from the left and right currents $i_L$ and $i_R$ as:

$$f(\theta) = \frac{i_L - i_R}{i_L + i_R}$$

The continuous nature of the intrinsic bulk 150 between the p-type electrodes 160 may cause in a resistance between each of the p-type electrodes 160 equivalent to an effective resistor $R_{eff}$ between the electrodes. The actual size of $R_{eff}$ may vary depending on the distance between the electrodes, the number of electrodes, the resistivity of the intrinsic bulk 150, the thickness of the intrinsic bulk 150, and a bias voltage $V_S$ applied to the substrate. A voltage source applying bias voltage $V_S$ may be coupled to substrate and may apply the bias voltage to the intrinsic bulk 150 to change a light detection sensitivity of the p-type electrodes 160 by altering the amount of light required to be absorbed in the intrinsic bulk 150 to generate an electron-hole pair.

The optical detector 100 may be designed to have a large $R_{eff}$ to suppress noise between circuits connected to each of the electrodes and to reduce Johnson noise. $R_{eff}$ may be made large by creating a substantial depletion region in the intrinsic bulk 150 around the p-type electrodes 160. This may be accomplished using a slightly n-type high resistivity intrinsic bulk 150 with p-type electrodes 160 to ensure a substantial depletion region around the electrodes. In other instances, a p-type intrinsic bulk 150 may be used with n-type p-type electrodes 160.

In some instances, the aperture and/or periphery may be positioned directly on top of the intrinsic bulk 150. In other instances, the intrinsic bulk 150 may be separated from the aperture and/or periphery by a transparent medium. The transparent medium may be a solid, liquid, or gas that is transparent and may include substances such as air, polymers, and glass. In some instances where the intrinsic bulk 150 is separated from the aperture and/or periphery, the periphery and/or aperture may be positioned at various heights above the intrinsic bulk 150, including but not limited to heights less than 30 microns and/or heights less than 10 microns.

The light angle sensor 100 need not include any lens or other devices that focus light. Thus, the aperture and medium need not focus the incident light 170 passing through them. By not including any lenses or other light focusing devices, it is possible to reduce the size and manufacturing costs and manufacturing time of the light angle sensor 100. The light detection efficiency of the light angle sensor 100 may, in some instance, be improved by using one or more lens to focus light on or below the continuous surface of the intrinsic bulk 150. In some instances, the aperture may be replaced with a lens.

Figure 2A:
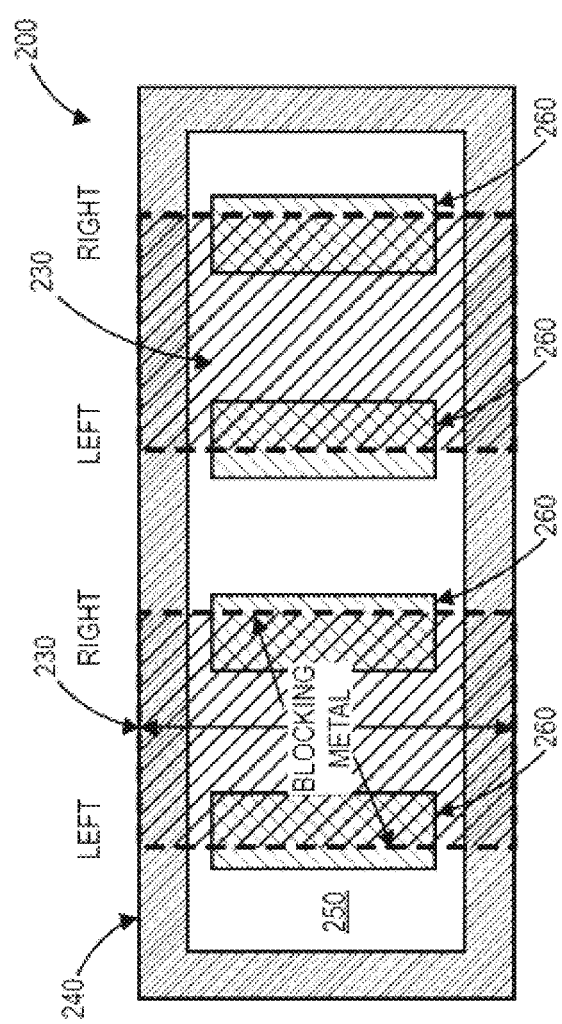
FIG. 2A shows an exemplary top-down view of a light angle sensor, in accordance with some embodiments of the disclosure provided herein.

FIG. 2A shows an exemplary top-down view of a light angle sensor 200, in accordance with one or more embodiments of the disclosure provided herein. Light angle sensor 200 comprises blocking metal 230, n-doped frame 240, p-type anodes 260, and intrinsic bulk 250. Left and right channels are bifurcated within the bulk, the operation of which will be discussed in greater detail later in the disclosure.

In one or more embodiments, the present disclosure aims to provide a photodiode sensor array and its fabrication method for an angle sensor based on using metal silicide as thin shadow metal to stop light entering between "Left" and "Right" photodiodes. This self-aligned device construction method uses a specific metal silicide, namely platinum silicide (PtSi) for the anode terminals. There are several choices when considering metals that are able to react with silicon to form silicides (Group IVA, VA, & VIA refractory and near-noble or noble metal silicides found in group VIII).

The choice of the silicide type is important in terms of device performance. Platinum is one of the few metals that is suitable based on its electrical performance, in terms of high conductivity, optical performance in terms of transmissivity and high temperature stability for sufficiently thick films. However, other metals and materials are not beyond the scope of the present invention.

In one or more embodiments, blocking metal comprises any optically opaque material. As would be understood by anyone skilled in the art, optically opaque doesn't necessarily mean the visible spectrum. As will be described later, light of longer wavelengths is frequently used. For example, near infrared (NIR) and midwave infrared (MWIR) can be used in light angle sensor 200. However, other wavelengths are not beyond the scope of the present disclosure.

In a preferred embodiment, blocking material is generally: conductive, substantially reflective, and/or substantially lossy beyond the penetration depth. That is, the material would have an imaginary part its complex impedance so as to largely prevent electromagnetic waves from passing therethrough, evanescent or otherwise.

In one or more embodiments, epitaxial bulk 250 comprising one or more epitaxially layers of intrinsic silicon. However, other epitaxial layer materials are not beyond the scope of the present invention. Epitaxy refers to a type of crystal growth or material deposition in which new crystalline layers are formed with a well-defined orientation with respect to the crystalline substrate. The new layers formed are called the epitaxial film or epitaxial layer.

The relative orientation of the epitaxial layer to the crystalline substrate is defined in terms of the orientation of the crystal lattice of each material. For epitaxial growth, the new layer will be crystalline and will all have a single orientation relative to the substrate; amorphous growth or multicrystalline growth with random crystal orientation does not meet this criterion.

In some embodiments, n-type frame 240 is a doped n-type semiconductor having an n-type group III material, such as, n-type GaN. However, other semiconductor materials are not beyond the scope of the present invention. N-type frame 240 can be made by adding an impurity to a pure semiconductor such as silicon or germanium. The impurities used may be phosphorus, arsenic, antimony, bismuth or some other chemical element.

In one or more embodiments, p-type electrodes 260 comprise p-type semiconductors. One or more trivalent impurities is added to an intrinsic or pure semiconductor (silicon or germanium), then it is said to be an p-type semiconductor. P-type electrodes 260 comprise trivalent impurities such as Boron (B), Gallium (Ga), Indium (In), Aluminum (Al), etc.

Figure 2B:
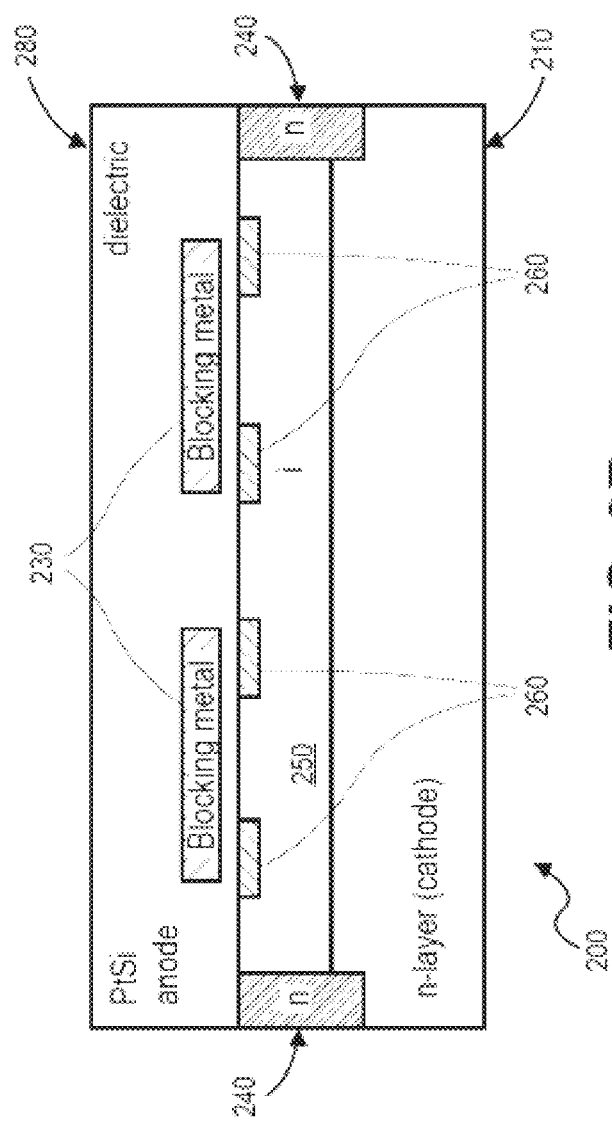
FIG. 2B shows an exemplary sideview of a light angle sensor, in accordance with some embodiments of the disclosure provided herein.

FIG. 2B shows an exemplary sideview of a light angle sensor 200, in accordance with one or more embodiments of the disclosure provided herein. Light angle sensor 200 comprises blocking metal 230, n-doped frame 240, p-type anodes 260, and intrinsic bulk 250, and n-layer substrate 210, and dielectric 280. In some embodiments, n-layer substrate 210 comprises n-type doped silicon and acts as a cathode which will be appreciated by those skilled in the art.

In practice, the p-type anodes 260, the intrinsic bulk 250, and n-type frame 240 are configured as a PIN diode which is used to collect light. A PIN diode is a diode with a wide, undoped intrinsic semiconductor region between a p-type semiconductor and an n-type semiconductor region. The p-type and n-type regions are typically heavily doped because they are used for ohmic contacts. The wide intrinsic region is in contrast to an ordinary p-n diode. The wide intrinsic region makes the PIN diode an inferior rectifier (one typical function of a diode), but it makes it suitable for attenuators, fast switches, photodetectors, and high voltage power electronics applications.

In some embodiments, a very thin layer of dialectic is laid down between blocking elements 230 and p-type electrodes, the importance of which will be discussed later in the disclosure. In some embodiments, p-type electrodes 260 comprise metal silicide. Specifically, p-type electrodes 260 can include platinum silicide (PtSi) for the anode terminals. In other embodiment there are several choices when considering metals that are able to react with silicon to form silicides (Group IVA, VA, & VIA refractory and near-noble or noble metal silicides found in group VIII), all of which are not beyond the scope of the present invention.

An object of the present disclosure is to have the electrodes block incident light. In particular, electrodes should be conductive, substantially reflective, and/or substantially lossy beyond the penetration depth. That is, the material would have an imaginary part its complex impedance so as to largely prevent electromagnetic waves from passing therethrough, evanescent or otherwise.

Figure 3A:
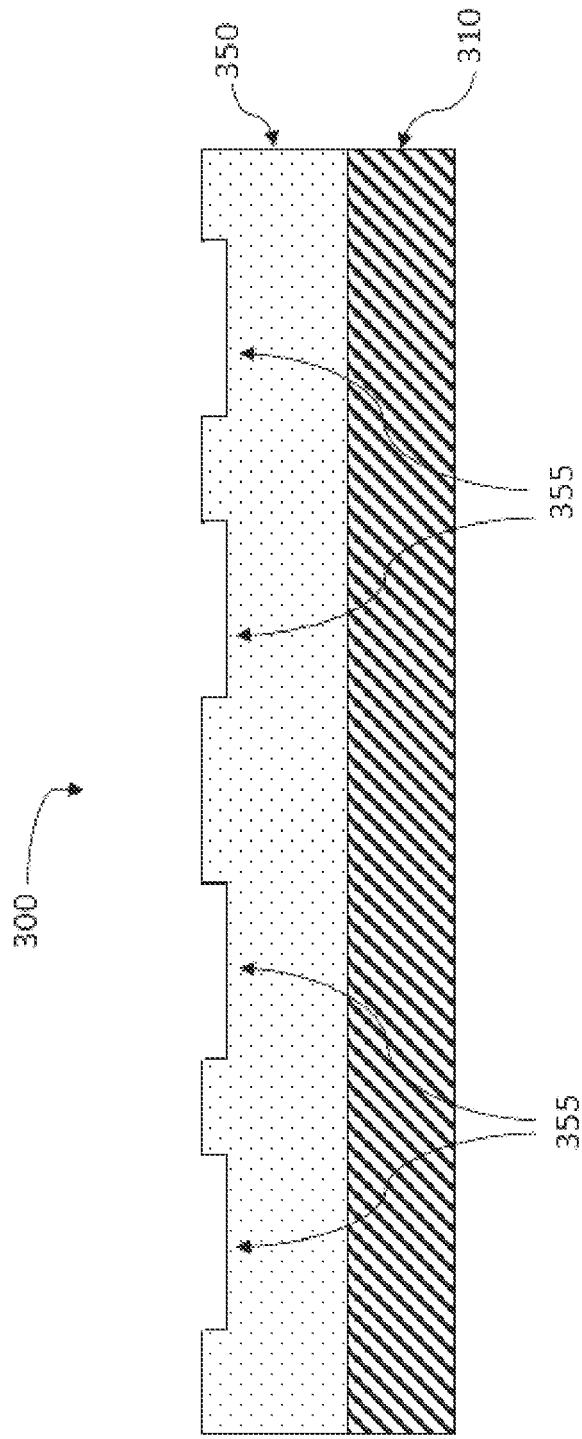
FIG. 3A demonstrates an exemplary sideview of a light angle sensor during fabrication, in accordance with some embodiments of the disclosure provided herein.

FIG. 3A demonstrates an exemplary sideview of a light angle sensor 300 during fabrication, in accordance with some embodiments of the disclosure provided herein. Light angle sensor 300 comprises substrate 310 and intrinsic layer 350.

In one or more embodiments, substrate 310 is an n-layer substrate which comprises n-type doped silicon and acts as a cathode. During fabrication, intrinsic layer 350 is epitaxially grown on substrate 310. In some embodiments, intrinsic layer 350 comprises silicon. Other materials, such as, Gallium Nitride, are not beyond the scope of the present disclosure.

In some embodiments, recesses 355 are etched into intrinsic layer 350. These recesses 355 are to be used to deposed electrodes which will be discussed in greater detail later in the disclosure. Specifically, part of a wafer is protected from the etchant by a "masking" material which resists etching. In some cases, the masking material is a photoresist which has been patterned using photolithography. Other situations require a more durable mask, such as silicon nitride. Wet etching, anisotropic wet etching (Orientation dependent etching), and plasma etching are within the scope of the present disclosure.

"Dry" (plasma) etching is used for circuit-defining steps, while "wet" etching (using chemical baths) is used mainly to clean wafers. Dry etching is one of the most frequently used processes in semiconductor manufacturing. Before etching begins, a wafer is coated with photoresist or a hard mask (usually oxide or nitride) and exposed to a circuit pattern during photolithography. Etching removes material only from the pattern traces. This sequence of patterning and etching is repeated multiple times during the chip making process.

Etch processes are referred to as conductor etch, dielectric etch, or polysilicon etch to indicate the types of films that are removed from the wafer. For example, dielectric etch is involved when an oxide layer is etched to leave "oxide isolators" separating devices from each other; polysilicon etch is used to create the gate in a transistor; dielectric etch is employed to etch via holes and trenches for metal conductive paths; and metal etch removes aluminum, tungsten, or copper layers to reveal the pattern of circuitry at progressively higher levels of the device structure.

Plasma etching is performed by applying electromagnetic energy (typically radio frequency, RF) to a gas containing a chemically reactive element, such as fluorine or chlorine. The plasma releases positively charged ions that bombard the wafer to remove (etch) materials and chemically reactive free radicals that react with the etched material to form volatile or nonvolatile byproducts. The electric charge of the ions directs them vertically toward the wafer. This produces the almost vertical etch profiles essential for the miniscule features in today's densely packed chip designs. Typically, high etch rates (amount of material removed in a given time) are desirable.

Figure 3B:
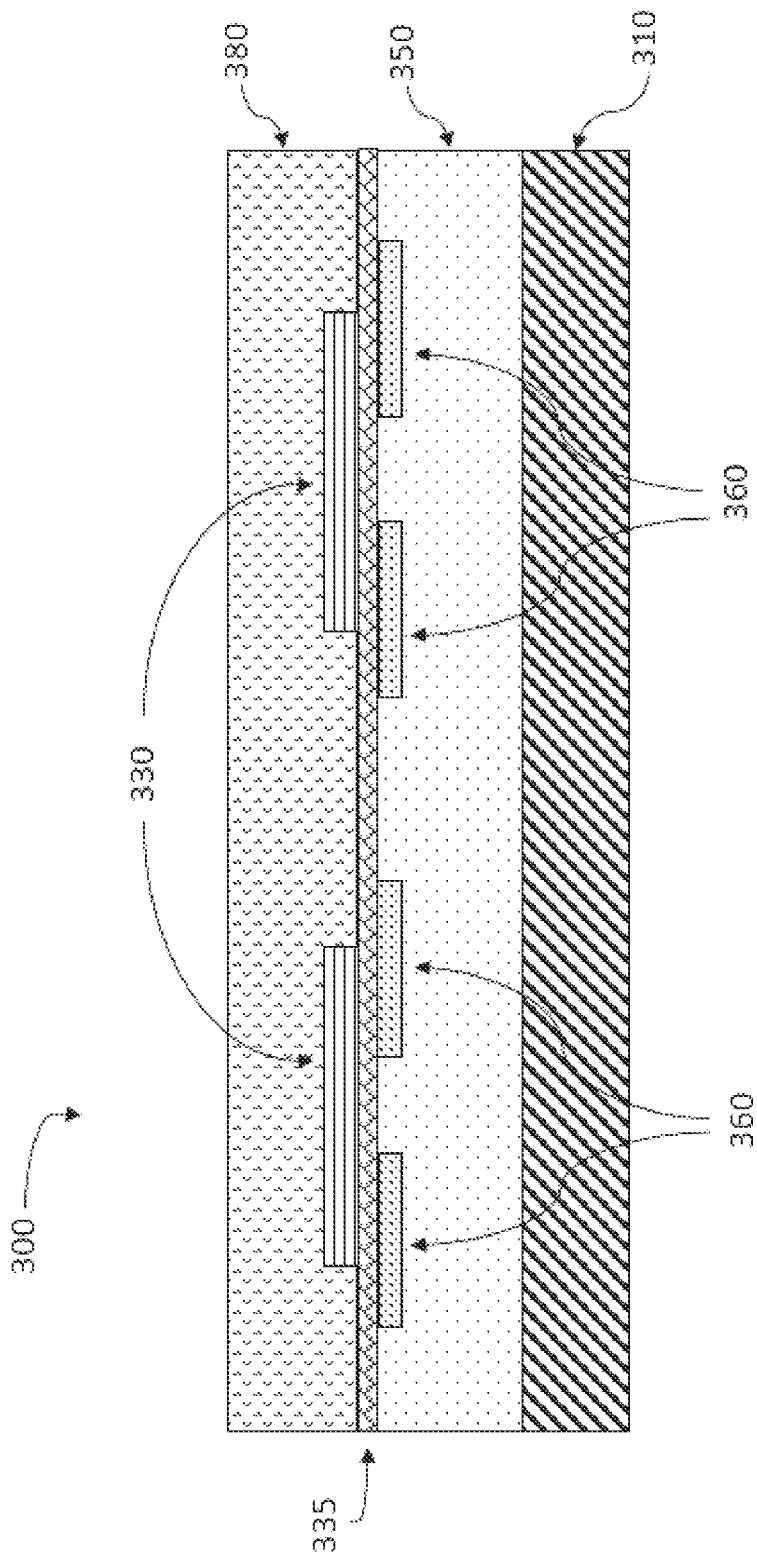
FIG. 3B demonstrates an exemplary sideview of a light angle sensor during fabrication, in accordance with one or more embodiments of the disclosure provided herein.

FIG. 3B demonstrates an exemplary sideview of a light angle sensor 300 during fabrication, in accordance with one or more embodiments of the disclosure provided herein.

Light angle sensor 300 comprises substrate 310, intrinsic layer 350, p-type electrodes 360, blocking member 330, passivation layer 335 and dielectric 380.

In one or more embodiments, substrate 310 is an n-layer substrate which comprises n-type doped silicon and acts as a cathode. However, in other embodiments, substrate 310 can p-type doped substrate acting as an anode. Intrinsic layer 350 is epitaxially grown on substrate 310. As discussed, intrinsic layer 350 doesn't necessarily have to be silicon. Other materials, such as, Gallium Nitride, are not beyond the scope of the present disclosure.

After etching pursuant to the discussion associated with FIG. 3A, p-type electrodes 360 are deposited into recesses 355. In one or more embodiments p-type electrodes 360 are thin metal silicide layers. In a preferred embodiment, these are platinum silicide (PtSi) for the anode terminals. A silicide is a compound that has silicon with (usually) more electropositive elements. Silicon is more electropositive than carbon. Silicides are structurally closer to borides than to carbides.

Similar to borides and carbides, the composition of silicides cannot be easily specified as covalent molecules. The chemical bonds in silicides range from conductive metal-like structures to covalent or ionic. Silicides of all non-transition metals, with exception of beryllium, have been described.

Platinum silicide, also known as platinum monosilicide, is the inorganic compound with the formula PtSi and forms an orthorhombic crystalline structure when synthesized. PtSi can be synthesized in several ways. In one or more methods, fabricating involves depositing a thin film of pure platinum onto silicon wafers (intrinsic layer 350) and heating in a conventional furnace at 450-600° C. for a half an hour in inert ambients. The process cannot be usually carried out in an oxygenated environment, as this results in the formation of an oxide layer on the silicon, preventing PtSi from forming.

In other embodiments, a secondary technique for synthesis requires a sputtered platinum film deposited on a silicon substrate. Due to the ease with which PtSi can become contaminated by oxygen, several variations of the methods have been reported. Rapid thermal processing has been shown to increase the purity of PtSi layers formed. Lower temperatures (200-450° C.) were also found to be successful, higher temperatures produce thicker PtSi layers, though temperatures in excess of 950° C. formed PtSi with increased resistivity due to clusters of large PtSi grains.

In practice, PtSi is a semiconductor and a Schottky barrier with high stability and good sensitivity, and can be used in infrared detection, thermal imaging, or ohmic and Schottky contacts. Platinum silicide has become less commonly used, due to its low quantum efficiency. In light sensors, PtSi is a desirable material due to the longer wavelengths it can be used to detect. PtSi can operate with good stability up to 0.05° C. Platinum silicide offers high uniformity of arrays imaged. The low cost and stability make it suited for preventative maintenance and scientific IR imaging.

In an alternate embodiment, p-type anodes 360 can be a salicide. The term salicide refers to a technology used in the microelectronics industry used to form electrical contacts between the semiconductor device and the supporting interconnect structure. The salicide process involves the reaction of a metal thin film with silicon in the active regions of the device, ultimately forming a metal silicide contact through a series of annealing and/or etch processes. The term "salicide" is a compaction of the phrase self-aligned silicide. The description "self-aligned" suggests that the contact formation does not require photolithography patterning processes, as opposed to a non-aligned technology such as polycide.

The term salicide is also used to refer to the metal silicide formed by the contact formation process, such as "platinum salicide", although this usage is inconsistent with accepted naming conventions in chemistry.

A passivation layer 335 is then applied to prevent short circuiting through blocking members 330. Passivation, in physical chemistry and engineering, refers to a material becoming "passive," that is, less affected or corroded by the environment of future use. Passivation involves creation of an outer layer of shield material that is applied as a microcoating, created by chemical reaction with the base material, or allowed to build from spontaneous oxidation in the air. As a technique, passivation is the use of a light coat of a protective material, such as metal oxide, to create a shell against corrosion. Passivation can occur only in certain conditions, and is used in microelectronics to enhance silicon.

The technique of passivation strengthens and preserves the appearance of metallics. In electrochemical treatment of water, passivation reduces the effectiveness of the treatment by increasing the circuit resistance, and active measures are typically used to overcome this effect, the most common being polarity reversal, which results in limited rejection of the fouling layer.

Blocking members 330 function to block the light which would ordinarily pass between p-type electrodes 360. This ameliorates crosstalk between the left and right channels. In some embodiments, dielectric 380 is applied on top of the passivation layer 335 and blocking members 330.

A dielectric (or dielectric material) is an electrical insulator that can be polarized by an applied electric field. When a dielectric material is placed in an electric field, electric charges do not flow through the material as they do in an electrical conductor but only slightly shift from their average equilibrium positions causing dielectric polarization. Because of dielectric polarization, positive charges are displaced in the direction of the field and negative charges shift in the direction opposite to the field (for example, if the field is moving in the positive x-axis, the negative charges will shift in the negative x-axis). This creates an internal electric field that reduces the overall field within the dielectric itself. If a dielectric is composed of weakly bonded molecules, those molecules not only become polarized, but also reorient so that their symmetry axes align to the field.

In some embodiments, dielectric 380 doesn't necessarily have to be made of a dielectric material. Any suitable material which is transparent or highly translucent at predetermined wavelengths can be used. The predetermined wavelengths are usually chosen from the illuminating device. For example, some light angle sensors use IR, near infrared (NIR), or midwave infrared (MWIR).

Figure 4A:
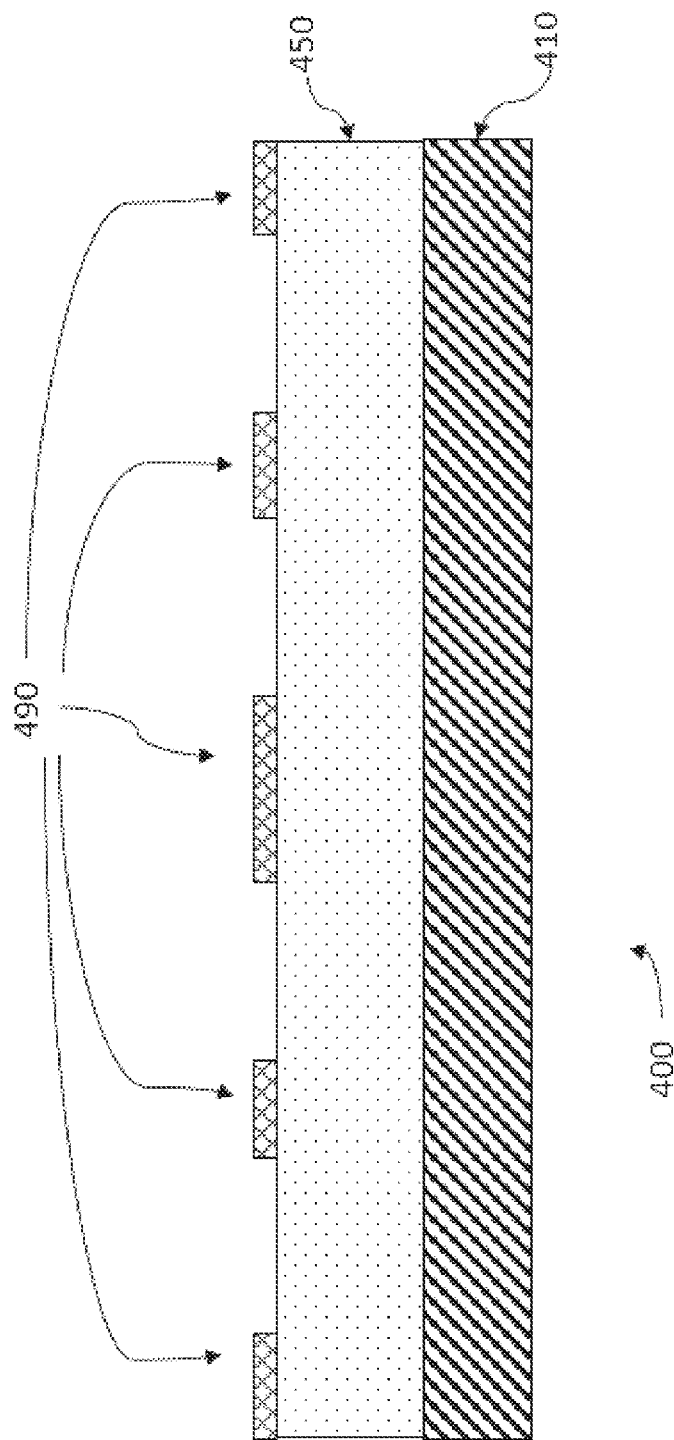
FIG. 4A demonstrates an exemplary sideview of a light angle sensor during an alternate fabrication process, in accordance with some embodiments of the disclosure provided herein.

FIG. 4A demonstrates an exemplary sideview of a light angle sensor 400 during an alternate fabrication process, in accordance with some embodiments of the disclosure provided herein. Light angle sensor 400 comprises substrate 410 and intrinsic layer 450. In the present embodiment, a sacrificial layer 490 is laid down. This is to be used to define the spaces for the PtSi electrodes. During fabrication, the sacrificial layer 490 is etched away using a suitable method known in the art, e.g., dry/plasma, wet, chemical, reactive ion, etc. In practice, FIG. 4A represents the cross-sectional view of the device defining the platinum-silicide anodes into the optical collection region.

Figure 4B:
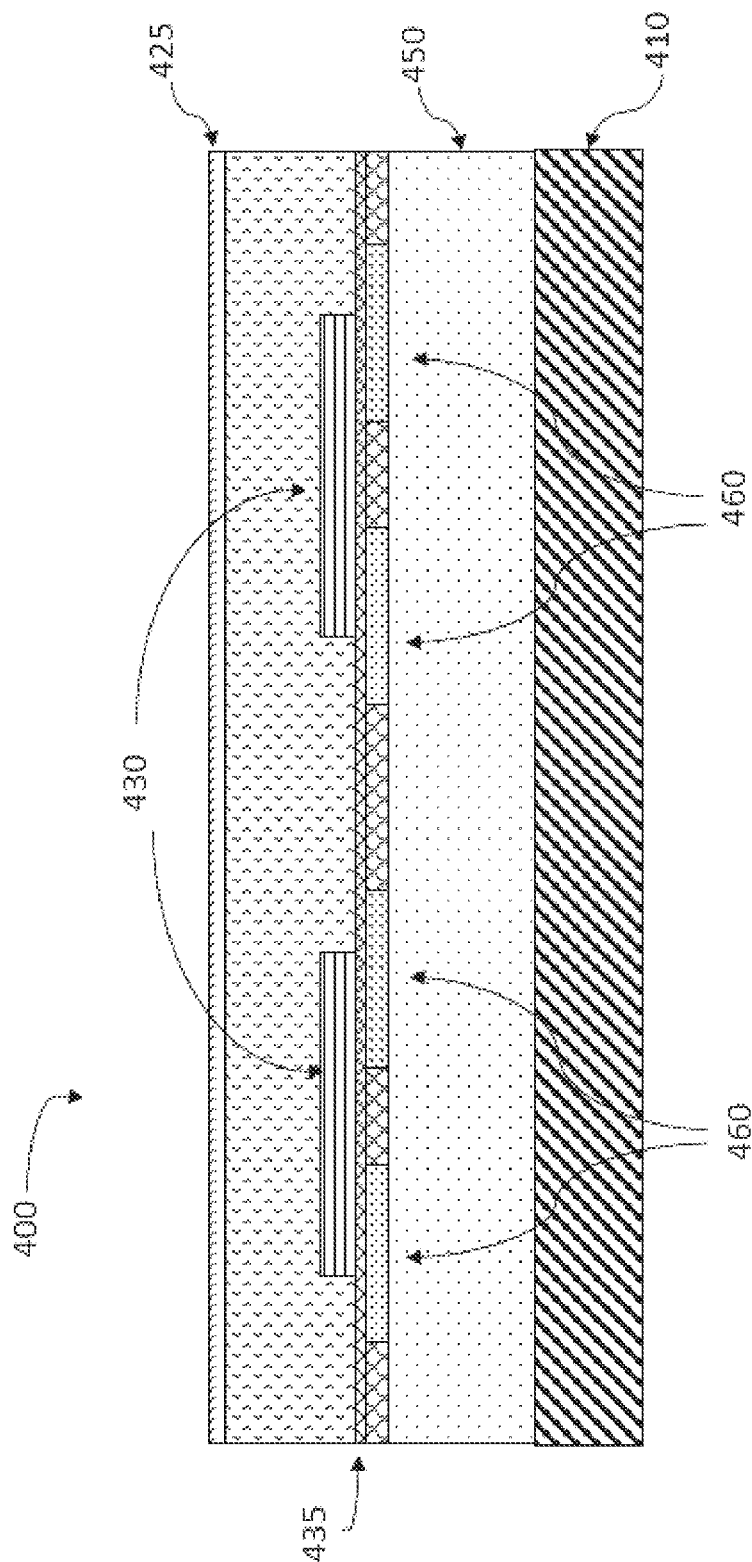
FIG. 4B demonstrates an exemplary sideview of a light angle sensor during fabrication, in accordance with one or more embodiments of the disclosure provided herein.

FIG. 4B demonstrates an exemplary sideview of a light angle sensor 400 during fabrication, in accordance with one or more embodiments of the disclosure provided herein. Light angle sensor 400 comprises substrate 410, intrinsic layer 450, p-type electrodes 460, blocking member 430, passivation layer 435, optical filter 425, and dielectric 480. In practice, FIG. 4B represents the cross-sectional view of the final device showing the metal light block, platinum-silicide anodes, the intrinsic layer for optical collection, the protective passivation layer, and the substrate, which serves as the photodiode cathode.

In one or more embodiments, substrate 410 is an n-layer substrate which comprises n-type doped silicon and acts as a cathode. However, in other embodiments, substrate 410 can p-type doped substrate acting as an anode. Intrinsic layer 450 is epitaxially grown on substrate 310. As discussed, intrinsic layer 450 doesn't necessarily have to be silicon. Other materials, such as, Gallium Nitride, are not beyond the scope of the present disclosure.

After etching pursuant to the discussion associated with FIG. 4A, p-type electrodes 460 are deposited into recesses created by sacrificial layer 490. In one or more embodiments p-type electrodes 460 are thin metal silicide layers. In a preferred embodiment, these are platinum silicide (PtSi) for the anode terminals.

A passivation layer 435 is then applied to prevent short circuiting through blocking members 430. Blocking members 430 function to block the light which would ordinarily pass between p-type electrodes 460. In some embodiments, dielectric 480 is applied on top of the passivation layer 435 and blocking members 430. In alternate embodiments, dielectric 380 doesn't necessarily have to be made of a dielectric material, as any suitable transmissive material is within the scope of the present disclosure.

In one or more embodiments, optical filter 425 is an interference filter. An interference filter consists of multiple thin layers of dielectric material having different refractive indices. There also may be metallic layers. In its broadest meaning, interference filters also comprise etalons that could be implemented as tunable interference filters. Interference filters are wavelength-selective by virtue of the interference effects that take place between the incident and reflected waves at the thin-film boundaries.

Depositions can be performed by, for example, but not limited to: direct metal deposition (DMD); laser metal deposition (LMD), thin-film deposition; chemical solution deposition (CSD), chemical bath deposition (CBD), chemical vapor deposition (CVD), plasma enhanced CVD (PECVD), atomic layer deposition (ALD), molecular layer deposition (MLD), physical vapor deposition (PVD), electroplating and sputtering.

In other embodiments, optical filter is a dichroic filter which can used for particular purpose, such as, those on the lenses which pass or block a band of predetermined wavelengths. Other optical filters are not beyond the scope of the present invention, such as, interference, absorption, diffraction, grating, Fabry-Perot, etc.

Figure 5A:
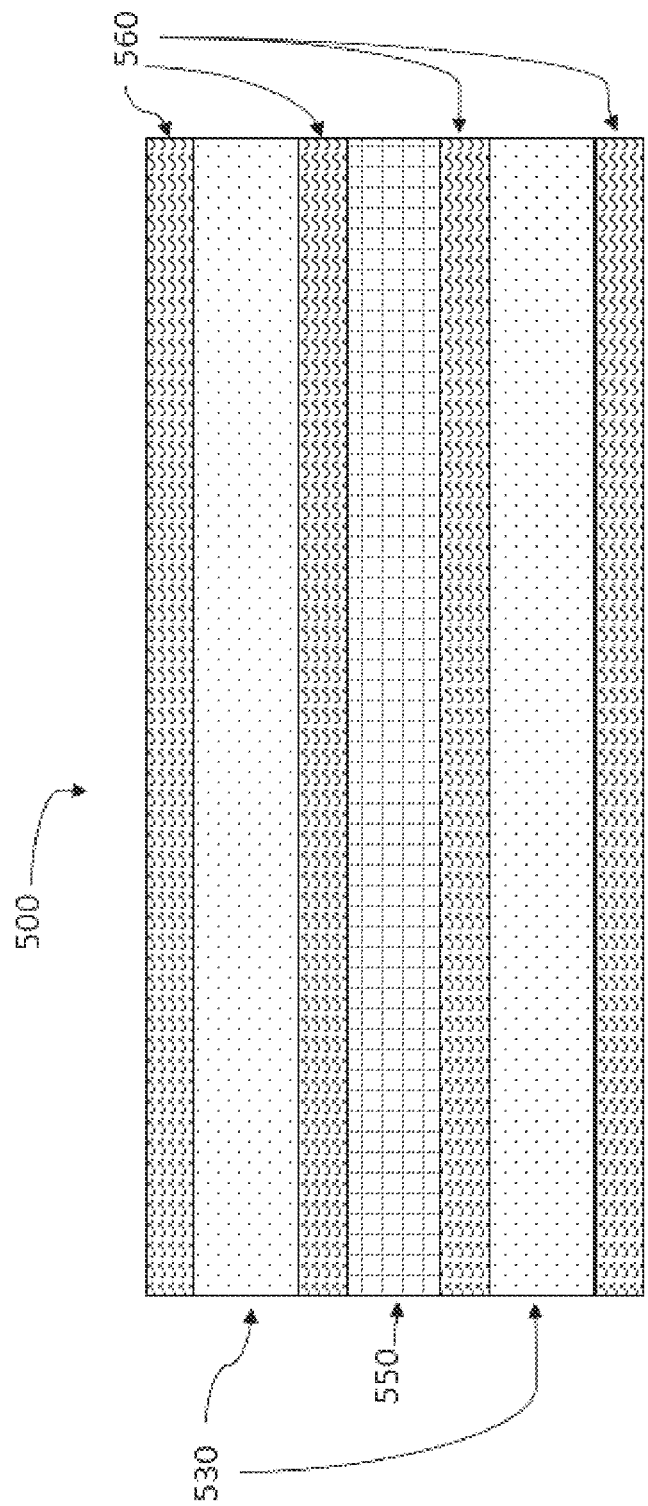
FIG. 5A shows an exemplary top-down view of a light angle sensor, in accordance with one or more embodiments of the disclosure provided herein.

FIG. 5A shows an exemplary top-down view of a light angle sensor 500, in accordance with one or more embodiments of the disclosure provided herein. Light angle sensor 500 comprises two photodiodes with a metal light blocks 530, platinum-silicide anodes 560, and intrinsic layer 550 for optical collection.

Figure 5B:
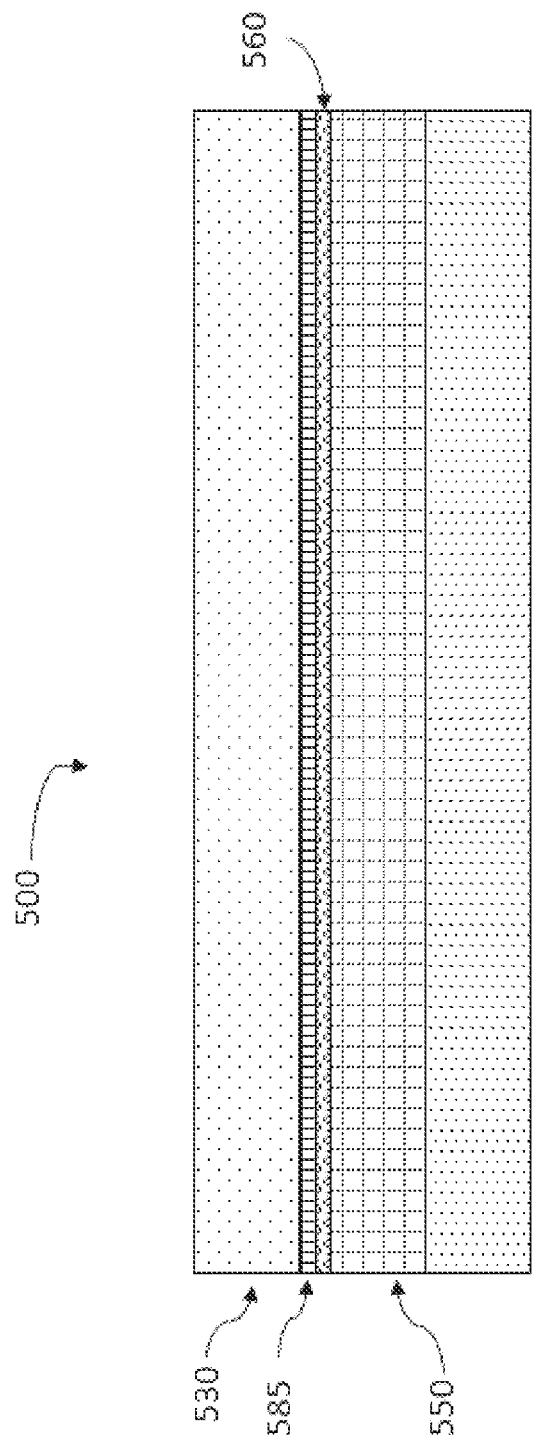
FIG. 5B shows an exemplary lengthwise view of a light angle sensor, in accordance with one or more embodiments of the disclosure provided herein.

FIG. 5B shows an exemplary lengthwise view of a light angle sensor 500, in accordance with one or more embodiments of the disclosure provided herein. FIG. 5B represents the cross-sectional view of the device with a metal light block 530, a thin silicided metal layer 560, a passivation layer 585 and intrinsic layer 550 for optical collection.

Figure 6:
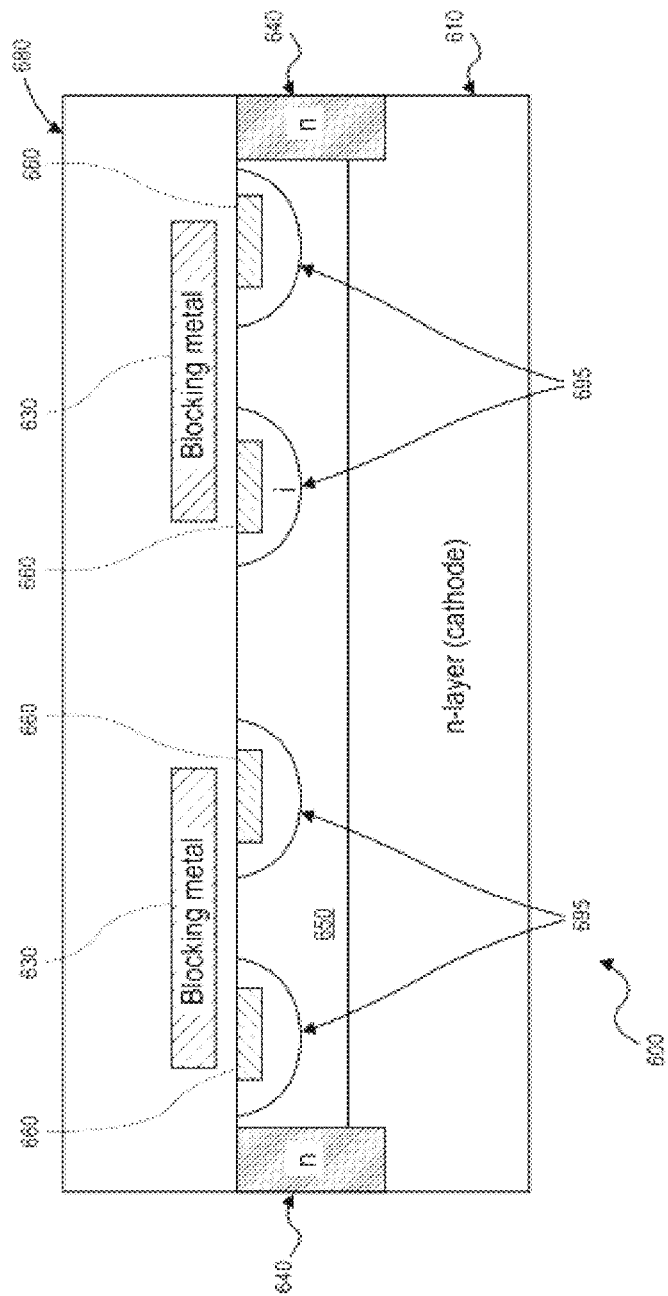
FIG. 6 illustrates an exemplary sideview of a biased light angle sensor, in accordance with one or more embodiments of the disclosure provided herein.

FIG. 6 illustrates an exemplary sideview of a biased light angle sensor 600, in accordance with one or more embodiments of the disclosure provided herein. Light angle sensor 600 comprises blocking metal 630, n-doped frame 640, p-type anodes 660, and intrinsic bulk 650, and n-layer substrate 610, and dielectric 680. In some embodiments, n-layer substrate 610 comprises n-type doped silicon and acts as a cathode which will be appreciated by those skilled in the art. In some embodiments, a very thin layer of dialectic is laid down between blocking elements 630 and p-type anodes 660.

In practice, the p-type anodes 660 are metal silicide anodes. They with the intrinsic bulk 650 and n-type frame 640 are configured as a PIN diode which is used to collect light. In operation, a depletion region 695 (also called depletion layer, depletion zone, junction region, space charge region or space charge layer) is an insulating region within a conductive, doped semiconductor material where the mobile charge carriers have been diffused away or have been forced away by an electric field. The only elements left in the depletion region are ionized donor or acceptor impurities.

A depletion region forms instantaneously across a p-n junction. It is most easily described when the junction is in thermal equilibrium or in a steady state: in both of these cases the properties of the system do not vary in time; they have been called dynamic equilibrium. Electrons and holes diffuse into regions with lower concentrations of them, much as ink diffuses into water until it is uniformly distributed.

By definition, the N-type semiconductor has an excess of free electrons (in the conduction band) compared to the P-type semiconductor, and the P-type has an excess of holes (in the valence band) compared to the N-type. Therefore, when N-doped and P-doped semiconductors are placed together to form a junction, free electrons in the N-side conduction band migrate (diffuse) into the P-side conduction band, and holes in the P-side valence band migrate into the N-side valence band.

Following transfer, the diffused electrons come into contact with holes and are eliminated by recombination in the P-side. Likewise, the diffused holes are recombined with free electrons so eliminated in the N-side. The net result is that the diffused electrons and holes are gone. In a N-side region near to the junction interface, free electrons in the conduction band are gone due to (1) the diffusion of electrons to the P-side and (2) recombination of electrons to holes that are diffused from the P-side. Holes in a P-side region near to the interface are also gone by a similar reason. As a result, majority charge carriers (free electrons for the N-type semiconductor, and holes for the P-type semiconductor) are depleted in the region around the junction interface, so this region is called the depletion region or depletion zone.

Due to the majority charge carrier diffusion described above, the depletion region is charged; the N-side of it is positively charged and the P-side of it is negatively charged. This creates an electric field that provides a force opposing the charge diffusion. When the electric field is sufficiently strong to cease further diffusion of holes and electrons, the depletion region reached the equilibrium. Integrating the electric field across the depletion region determines what is called the built-in voltage (also called the junction voltage or barrier voltage or contact potential).

In operation, depletion region 695 can be changed as a function of the bias applied to the circuit (i.e., PIN). For example, depletion region 695 can be augmented by a larger reverse bias. This increases both photon collection width and potential depth of the photon collection area in the intrinsic bulk 650. This results in effecting a more sensitive light angle sensor 600. As one skilled in the art, the desirable condition is compounded by lack of doping in the bulk 650 which also augments the photon collection width and potential depth of the photon collection area.

Figure 7:
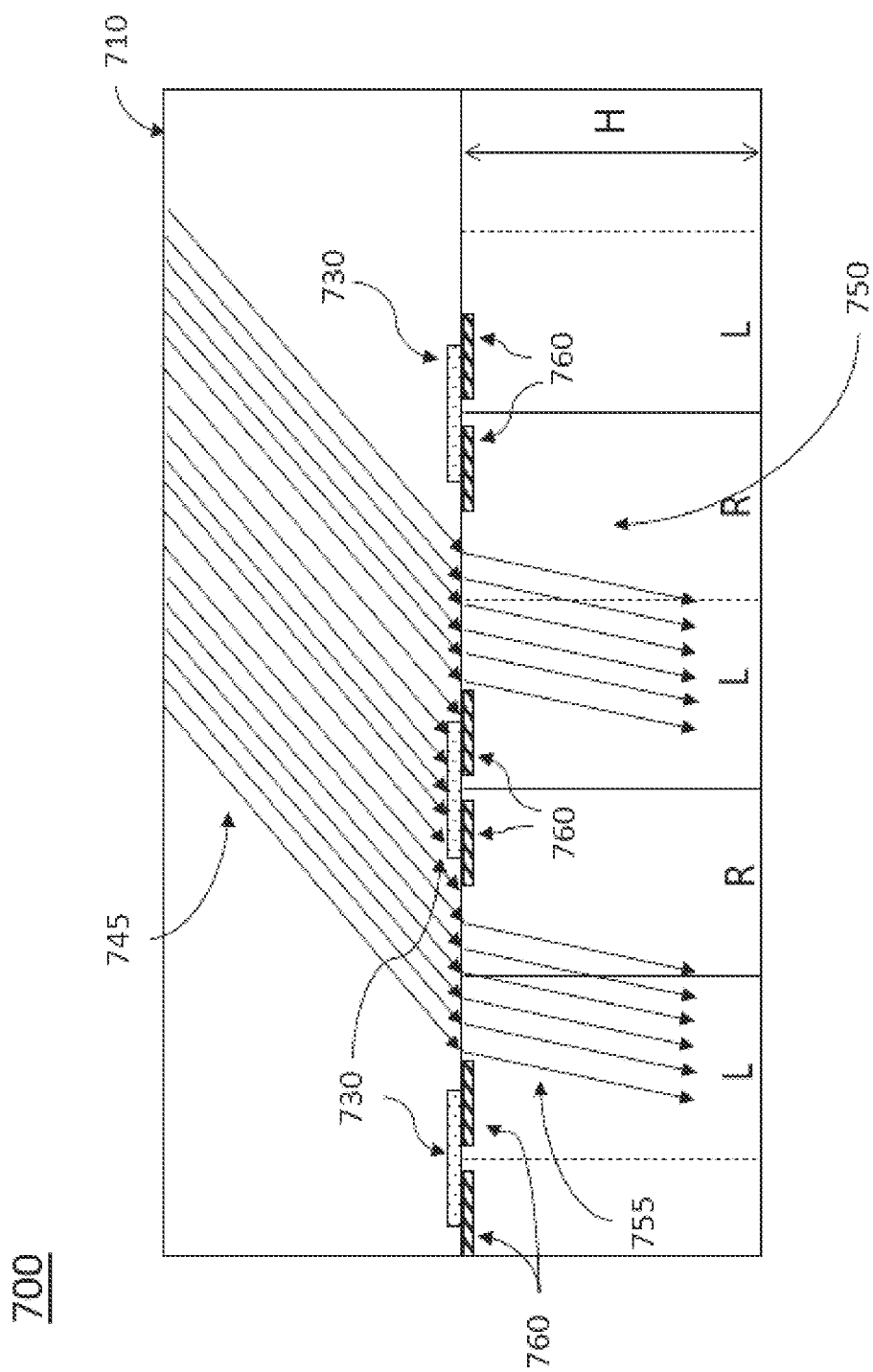
FIG. 7 illustrates an exemplary sideview of a light angle sensor, in operation and in accordance with one or more embodiments of the disclosure provided herein.

FIG. 7 illustrates an exemplary sideview of a light angle sensor 70, in operation and in accordance with one or more embodiments of the disclosure provided herein. Light angle sensor 700 comprises blocking metal 730, n-doped frame 740, p-type anodes 760, and intrinsic bulk 750, and dielectric 710. In operation, FIG. 7 represents light ray traces of incident light demonstrating how light collection is proportional to the angle of incident light upon the set of "left" versus "right" photodiodes.

In practice, the p-type anodes 760 are metal silicide anodes. They with the intrinsic bulk 750 and n-type frame 740 are configured as a PIN diode which is used to collect light. In operation, light 745 impinges on dielectric 710 at an arbitrary first angle. Light 745 then passes through dielectric 710 and is incident on the face on the intrinsic bulk 750 and passes therein at a second angle. As in known in the art, the second angle is a function of the first angle and the two indices of refraction of the two materials, dielectric 710 and intrinsic bulk 750.

Further in operation, left ("L") and right ("R") photodetectors each having a p-n junctions which converts light 745 photons into current. The absorbed photons create electron-hole pairs in the depletion region. As previously described, a ratio (or any comparison really) can be measured between L/R channels and an angle of incident can be determined therefrom. It is noted that in the present disclosure, no calibration is necessary at the factory. This is contrary to the state of the art which either requires calibration, registration or both.

In some embodiments, a very thin layer of dialectic is laid down between blocking elements 730 and p-type anodes 760. The object of the thinness is to mitigating any light passing therebetween which might improperly detected at an adjacent channel. Creating a very thin boundary will maintain electrical insulation while minimizing the ingress "aperture." It will also ensure maximizing internal reflections between blocking elements 730 and p-type anodes 760 which causes the light to die off through scattering and/or absorption.

Figure 8:
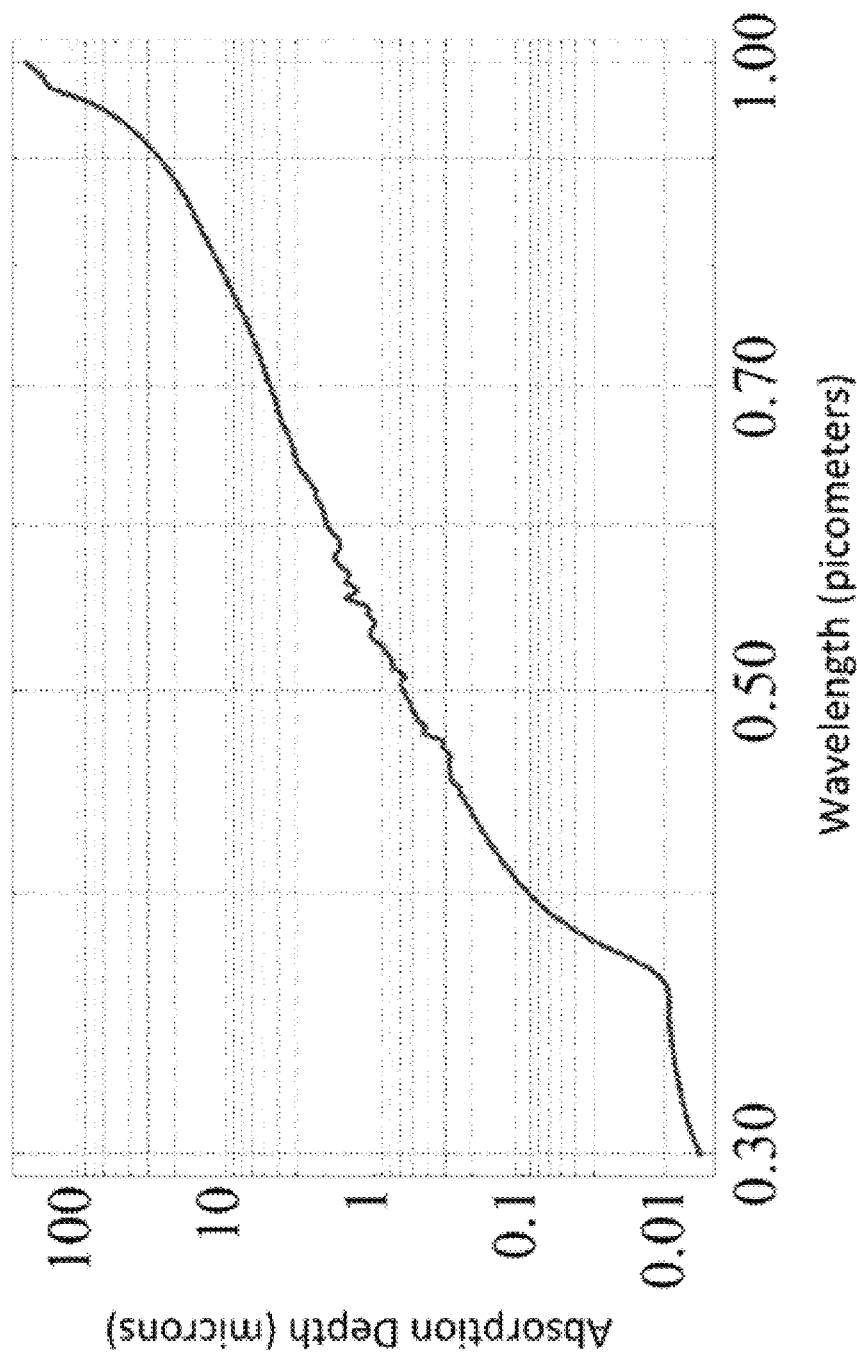
FIG. 8 shows an exemplary graph of light absorption depths at different wavelengths in a silicon substrate within a light angle sensor, in accordance with one or more embodiments of the disclosure provided herein.

FIG. 8 shows an exemplary graph of light absorption depths at different wavelengths in a silicon substrate within a light angle sensor, in accordance with one or more embodiments of the disclosure provided herein. In many semiconductors, including indirect bandgap semiconductors such as silicon or germanium semiconductors, the absorption depth of incident light 120 is a function of the wavelength of the light 120.

FIG. 8 shows an exemplary light absorption depth chart in silicon semiconductors for different wavelengths of the light. As shown in FIG. 8, much of the visible light spectrum from 350 nm to 700 nm is absorbed in a relatively shallow region of few microns. However, near infrared (NIR) light, such as that emitted from a remote controller LED at 850 nm or 940 nm is absorbed relatively deeply. Making the epitaxial layer deep enough to collect a large fraction of this NIR light may result in electrodes collecting a substantial fraction of the NIR light but practically none of visible light. Varying the bias of the electrodes may in turn further change the probability that the different colors and wavelengths of light are collected by each of the electrodes.

In some instances, the relative amount of photocurrents generated at the electrodes may be used to calculate an amount of ambient light, such as the light seen by a human eye.

Figure 9:
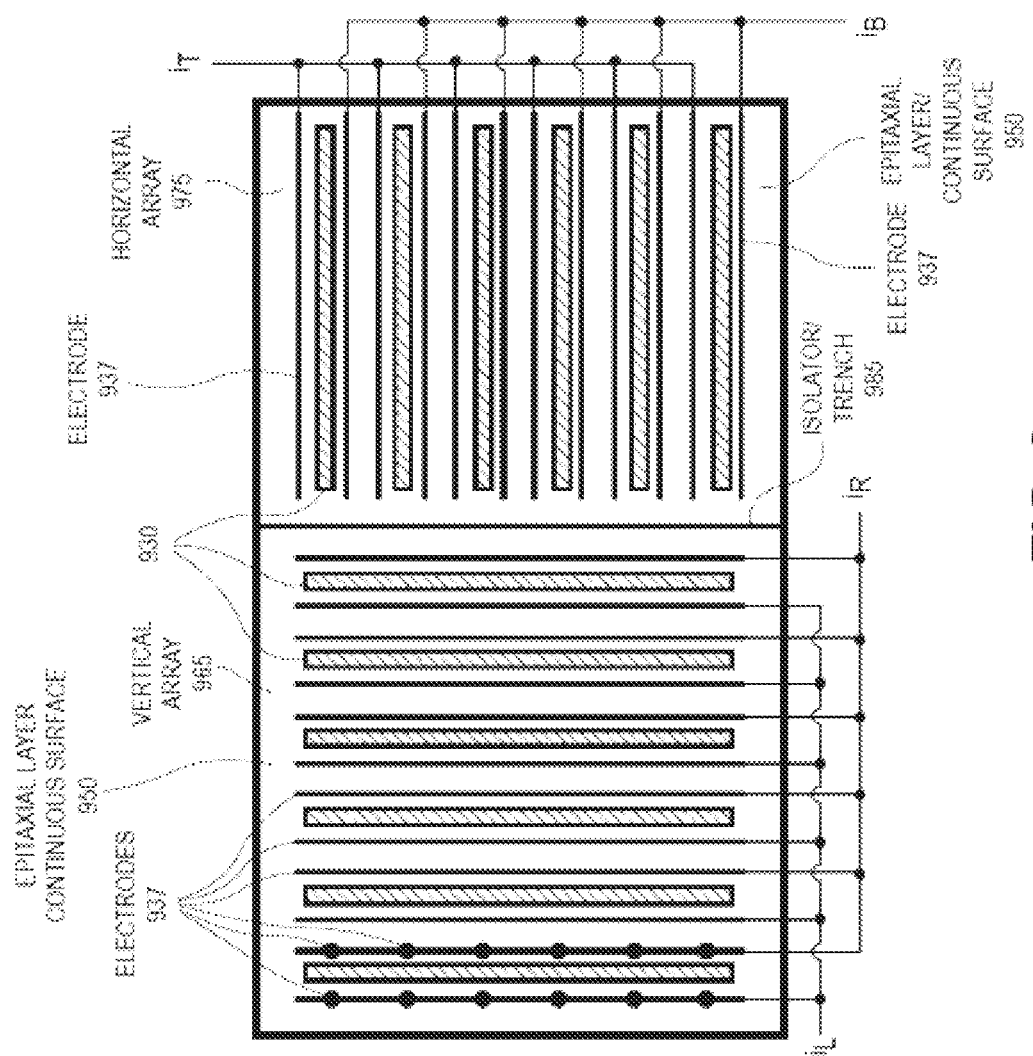
FIG. 9 shows an exemplary top-view perspective of a second two-dimensional optical detector in an embodiment of the disclosure provided herein.

FIG. 9 shows an exemplary top-view perspective of a second two-dimensional optical detector in an embodiment of the disclosure provided herein. FIG. 9 shows an embodiment of a light angle sensor including both a vertical array 965 and a horizontal array 975 which straddle blocking members 930 and corresponding sets of electrodes 937. FIG. 9 shows six exemplary vertical L/R channels in the vertical array 965 and six exemplary horizontal U/D (up/down) channels in the horizontal array 975. Each of the channel pairs may have a set of one or more electrodes positioned parallel to the blocking members 930 along a longitudinal direction of the blocking members on both sides.

The blocking members 930 may also have beveled edges pointing away from the epitaxial layer 950 to minimize the likelihood that the incident light will be reflected off the edge and redirected onto the epitaxial layer 950. Each electrode 937 may be arranged in the epitaxial layer 950 to detect a respective quantity of the incident light passing through each space.

Some of the electrodes 937 may be rectangularly shaped and extend longitudinally for at least a similar distance as the respective blocking members 930 associated with the electrode 937. Some of the electrodes 937 may also be positioned parallel to its associated blocking member 930, and in some instances, pairs of these electrodes 937 may be positioned at equal distances from and on either side of the associated blocking member 930 as shown in FIGS. 3-4. Each pair of these electrodes 937 may also be centered with a center of its corresponding blocking member 930. In other instances, one or more electrodes or electrodes pairs may be offset from a center of its corresponding blocking members 930.

In some instances, the electrodes 937 may include several point electrodes such as those shown parallel to both longitudinal sides of the left most blocking member 930. The point electrodes may be positioned along two or more imaginary lines oriented parallel to the blocking members 930. In the example shown in FIG. 9, the two imaginary lines are running vertically along both sides of the left most blocking member 930. Respective point electrodes running along each imaginary line associated with a particular aperture may be electrically coupled together.

The vertical blocking members 930 in the vertical array 965 may be arranged parallel to each other and perpendicular to the horizontal blocking members 930 in the horizontal array 975. Different electrodes 937 associated with different blocking members 930 may be coupled together provided that the orientation of the electrode 937 with respect to its corresponding blocking member is similar.

For example, as shown in FIG. 9, all of the electrodes located on the left side of different blocking members 930 may be electrically coupled to generate an aggregated left current $i_L$ and increase the light detection efficiency of the light angle sensor. Similarly, all the electrodes on the right side, top side, and bottom side of the blocking members 930 may also be coupled together to generate aggregate right $i_R$, top IT, and bottom $i_B$ currents and further increase the light detection efficiency.

In some instances, an electrical signal isolator 985 may be inserted or formed in the epitaxial layer 950 to subdivide the epitaxial layer 950 into multiple separate continuous surfaces. The isolator 985 may surround one or more electrodes 937 to isolate the ability of the electrodes 937 to collect only those electron-hole pairs that are generated within the isolated region surrounding the electrode 937.

In some instances the isolator 985 may be used to compartmentalize the epitaxial layer 950 around each set of electrodes associated with each blocking member so that the quality of light reaching the epitaxial layer 950 that is detectable by a respective electrode 937 is isolated to only the incident light that actually passes through the local space. In the example shown in FIG. 9, the isolator 985 is a trench that subdivides the epitaxial layer 950 into two continuous sections, a first section encompasses the electrodes 937 in the vertical array 965 and a second section encompasses the electrodes 937 in the horizontal array 975.

Figure 10:
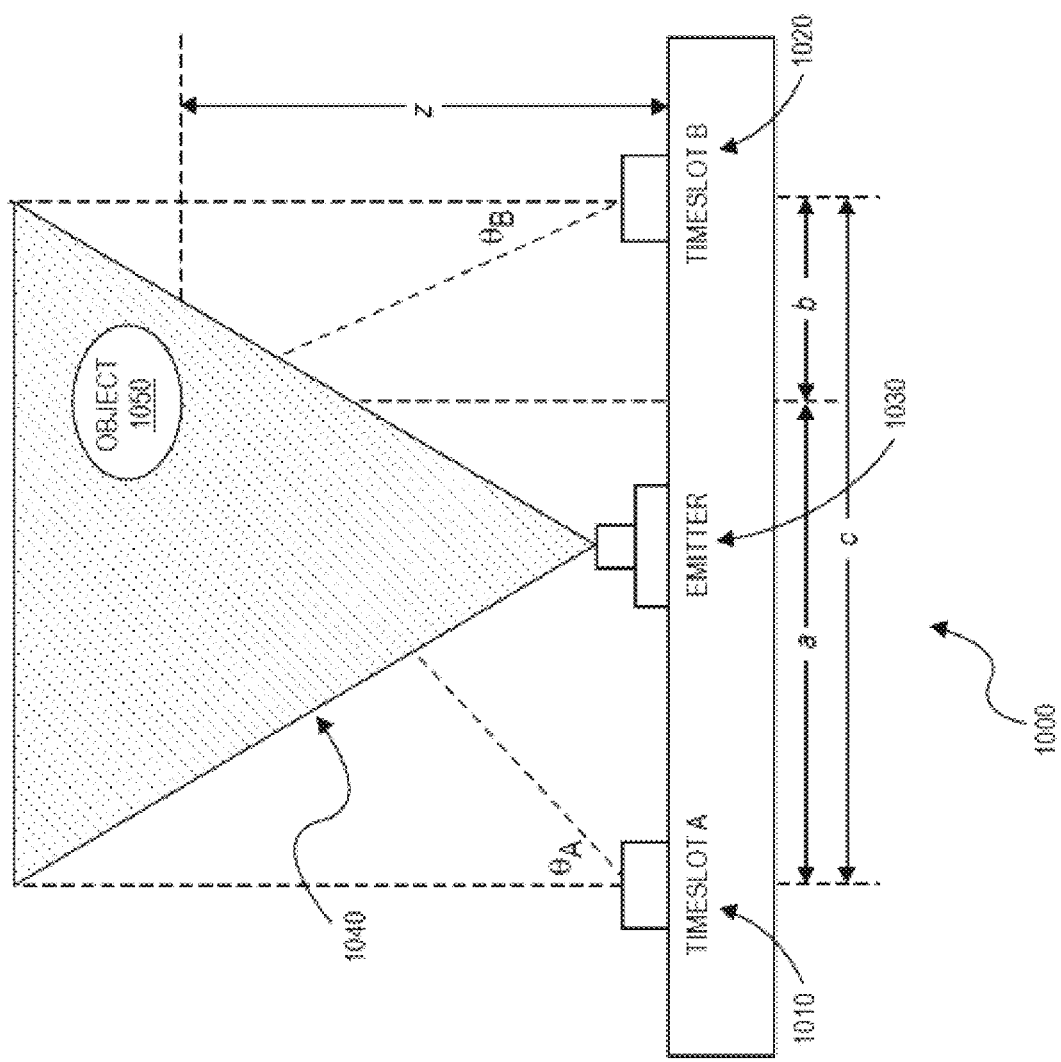
FIG. 10 depicts shows an exemplary application in which a lens-less optical detector may be used to track movement of an object or device in multiple dimensions based on emitted light that is reflected off the object, in accordance to one or more embodiments of the present disclosure provided herein.

FIG. 10 depicts shows an exemplary application in which a lens-less optical detector 1000 may be used to track movement of an object or device in multiple dimensions based on emitted light that is reflected off the object, in accordance to one or more embodiments of the present disclosure provided herein. Optical detector 1000 comprises light angle sensor 1010, light angle sensor 1020, and emitter 1030.

In one or more embodiments, emitter 1030 comprises a MWIR LED which projects a conical light cone 1040 having an outer diverging angle of approximately 20 degrees. In operation, the specific location of object 1050 may be determined by simple geometry. Light angle sensor 1010 measures OA and light angle sensor 1020 measures OB whereby parameters a, b, c, and distance z can be calculated by one of any skill in the art.

Turning to FIG. 10, the present embodiment shows how an object may be tracked based on emitted light 104 that is reflected off the object 1050. In this example, one or more light sources, such as emitter 1030 may be uniquely modulated into a region of space. When an object 1050 enters the region of the space, the emitted light may be reflected off the object and strike the photodetectors in sensors in light angle sensor 1010 and light angle sensor 1020. Each sensor may include photodetectors and/or photodetector arrays similar to those shown in the preceding figures. Each sensor may also be configured to identify the uniquely modulated light waves from one or more of the light sources.

As discussed previously, the photocurrents from each of the photodetectors in sensors may be used to determine an angle of the reflected light detected at the sensors in light angle sensor 1010 and light angle sensor 1020. A position of the object 1050 may then be calculated from the angles of the reflected light using geometry and/or triangulation.

Thus, embodiments of the invention may be used in cars as parking sensors or pedestrian detection devices to alert a driver of objects 1050, such as pedestrians, trees, or other cars, that may be in the vicinity of the vehicle. Embodiments may also be used in electronic devices, such as smartphones, computers, and tablets to detect a presence or movement of an object, such as a finger. Embodiments may also be used to provide similar functionality to that of a trackball, touchpad, or mouse by tracking the movement of a finger or other object, such as a mouse. Embodiments may also be used to detect movement and provide robotic control over moving parts.

Lens-less sensors may also provide increased response times and sensitivity to changes in an intensity of detected light over traditional lens-based sensors. Lens-less sensors may also be capable of detecting light on much larger detector surfaces than lens-based sensors. These properties enable lens-less sensors to support data communications at high frequencies using modulated light in the hundreds of kilohertz to gigahertz range that may be transmitted through air.

Other devices are beyond the scope of the present disclosure. For example, other light sources, such as, broadband lamps, incoherent bulb, lasers, and coherent, etc., all can be used. Additionally, while a color greater than 1 μm is preferable when using a silicon bulk, other colors are also within the context and intent of the present disclosure.

Figure 11:
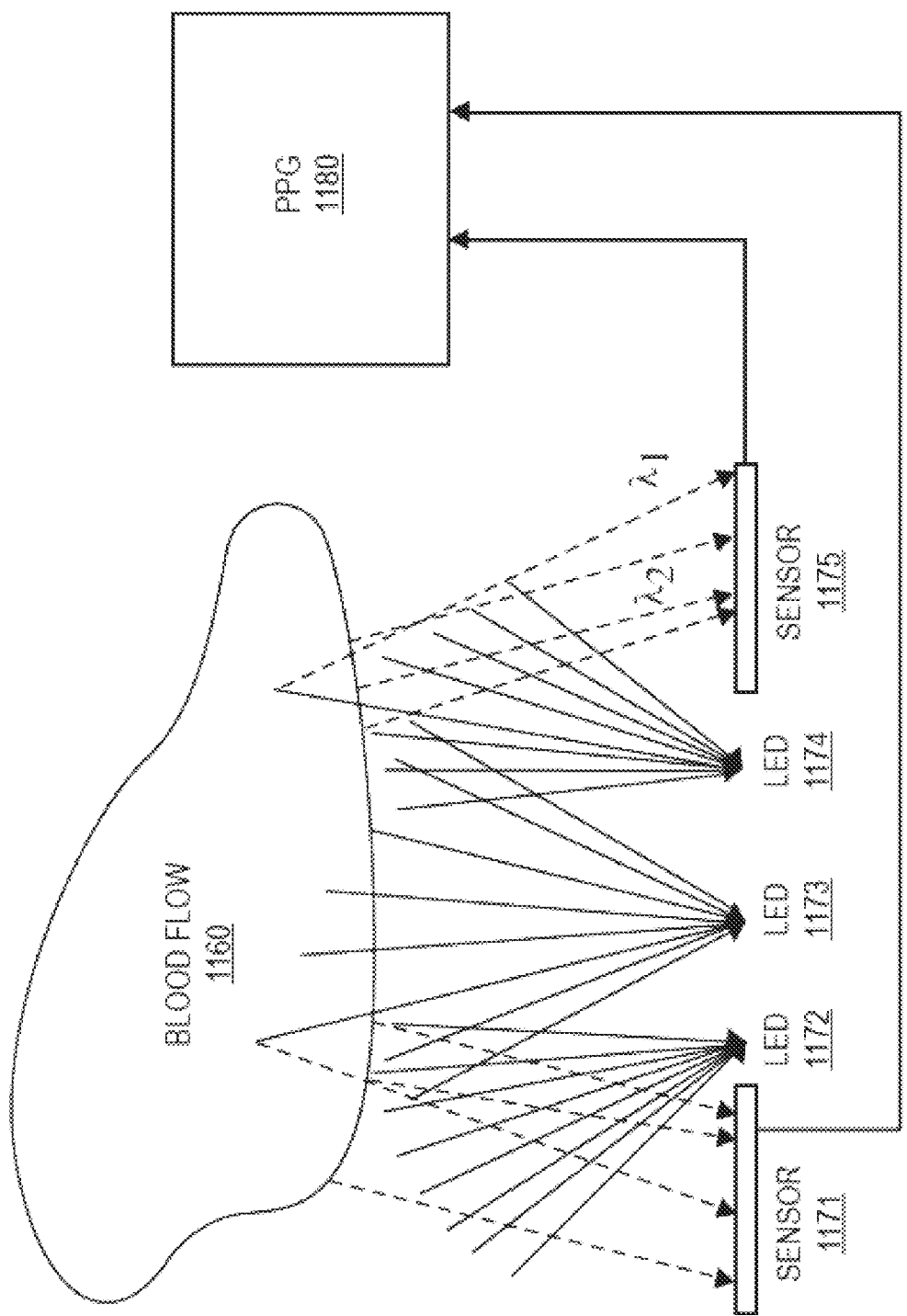
FIG. 11 depicts shows an exemplary application in which spectrometric information about an object may be measured based on emitted light passed through or reflected off the object, in accordance to one or more embodiments of the present disclosure provided herein.

FIG. 11 depicts shows an exemplary application in which spectrometric information about an object may be measured based on emitted light passed through or reflected off the object, in accordance to one or more embodiments of the present disclosure provided herein.

In some embodiments, spectrometric information about an object can be measured in addition to the spatial information described previously. For example, blood oxygen levels may be measured using two colors of light (there are many choices but wavelengths near 660 nm and 940 nm are often selected) to perform a spectrometry on the blood inside the body. A heart rate, photoplethysmograph (PPG), and other oximetry measurements may be obtained from light detected at the lens-less sensor after passing through or being reflected off a blood flow in a person or animal.

FIG. 11 shows an example embodiment in a PPG 1180 for an object 1160 can be measured. In this example, one or more light sources, such as LEDs 1172, 1173, and 1174, may be uniquely modulated into a region of space. When an object, for example an object with blood flow 1160, enters the region of the space, the emitted light may be reflected off or pass through the blood flow 1160 and strike the photodetectors in sensors 1171 and 1175.

Each sensor 1171 and 1175 may include photodetectors and/or photodetector arrays similar to those shown in the preceding figures. Each sensor 1171 and 1175 may also be configured to identify the uniquely modulated light waves from one or more of the light sources 1172, 1173, and 1174. As discussed previously, the photocurrents from each of the photodetectors in sensors 1171 and 1175 may be used to determine an angle of the reflected light detected at the sensors 1171 and 1175. A PPG 1180 of the object having blood flow 1160 may then be calculated based on wavelengths $\lambda_1$, $\lambda_2$ of the received light.

PPG signals for pulse oximetry may be measured by calculating a DC signal level and an AC amplitude of the photocurrents from the detected light at each of the two wavelengths, $\lambda_1$, $\lambda_2$, after passing through or being reflected off a blood flow in a person or animal. The following ratio may be used to measure saturated blood oxygen:

$$R = \frac{(I_{AC}/I_{DC})\lambda_1}{(I_{AC}/I_{DC})\lambda_2}$$

The connection between R and the actual blood oxygen may be based on simple physical theory or an empirically measured fit between R and blood oxygen levels. This medical information may be provided in an embodiment in conjunction with object tracking and/or spatial positioning functionality.

Figure 12:
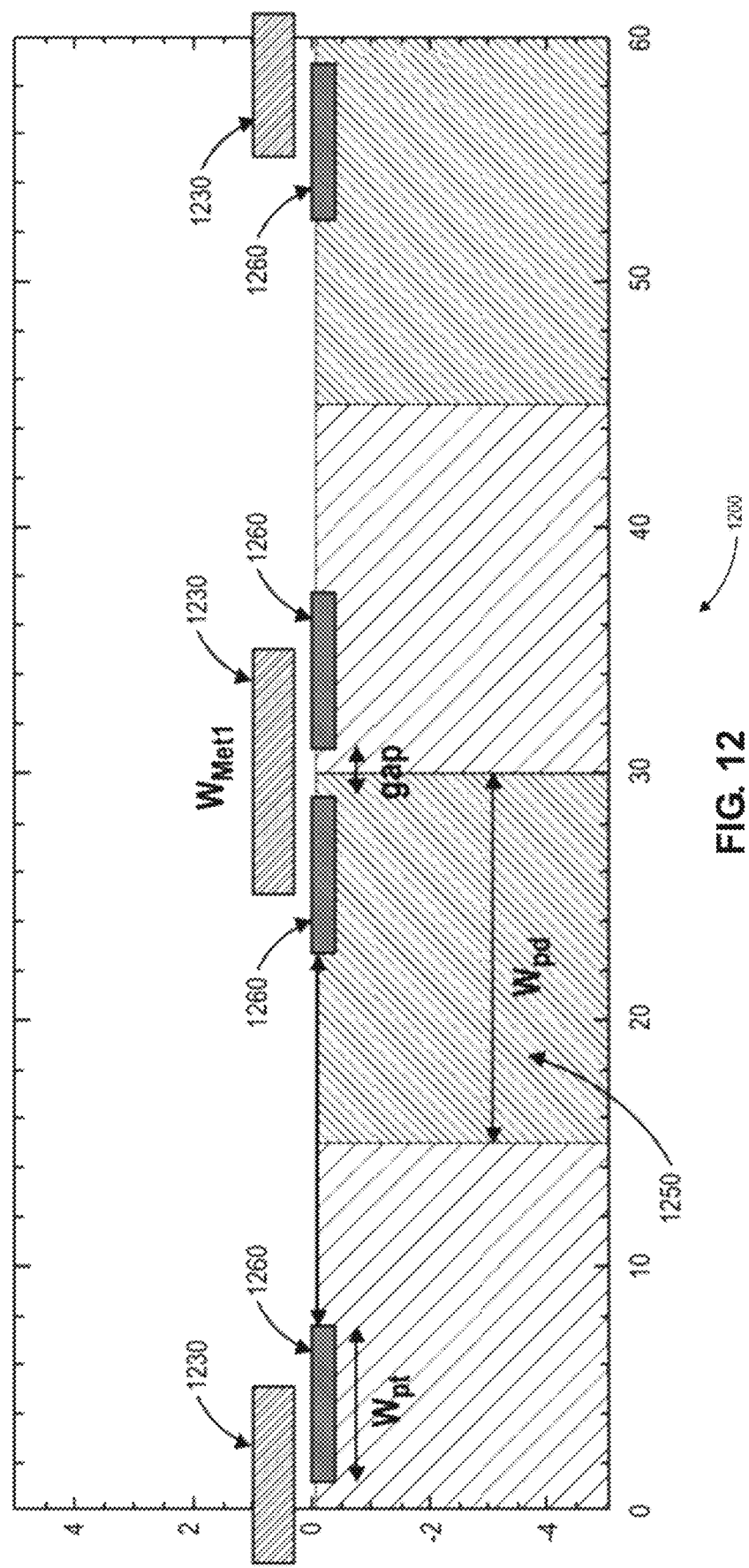
FIG. 12 illustrates an exemplary sideview of a light angle sensor, in operation and in accordance with an alternate embodiment of the disclosure provided herein.

FIG. 12 illustrates an exemplary sideview of a light angle sensor 1200, in operation and in accordance with an alternate embodiment of the disclosure provided herein. Light angle sensor 1200 comprises blocking layers 1230, p-type anodes 1260, and intrinsic bulk 1250, and p-layer substrate 1210. In some embodiments, n-layer substrate 1210 comprises n-type doped silicon and acts as a cathode which will be appreciated by those skilled in the art.

In practice, the p-type anodes 1260, the intrinsic bulk 1250, and n-layer substrate 1210 are configured as a PIN diode which is used to collect light. A PIN diode is a diode with a wide, undoped intrinsic semiconductor region between a p-type semiconductor and an n-type semiconductor region. The p-type and n-type regions are typically heavily doped because they are used for ohmic contacts. The wide intrinsic region is in contrast to an ordinary p-n diode.

An object of the present disclosure is to have the electrodes block incident light. In particular, electrodes should be conductive, substantially reflective, and/or substantially lossy beyond the penetration depth. That is, the material would have an imaginary part its complex impedance so as to largely prevent electromagnetic waves from passing therethrough, evanescent or otherwise.

Turning to FIG. 12, the units are in µm. In one or more embodiments, the following relation holds, also in µm:

$$W_{Pt} = \frac{S_{open}}{2} - \frac{gap}{2}$$

$$W_{Met1} = W_{pd} - 5$$

The gap can be set at 2 um, but will vary depending on the application. Blocking layers 1230 are approximately 4.5× a passivation layer disposed in between the blocking layers 1230 and p-type anodes 1260, as previously described.

The foregoing description has been presented for purposes of illustration and description. It is not exhaustive and does not limit embodiments of the invention to the precise forms disclosed. Modifications and variations are possible in light of the above teachings or may be acquired from the practicing embodiments consistent with the invention. For example, some of the described embodiments discuss the use of horizontally and vertically aligned light angle sensors and/or photodetector arrays, but in other embodiments, some of the light angle sensors and/or photodetectors may be aligned in other non-horizontal and non-vertical orientations.

Furthermore, alternate materials and devices are not beyond the scope of the present invention. For example, the epitaxial layers may be germanium based or other suitable material in some instances, rather than silicon.

Similarly, metal silicides can be replaced with a more traditional Schottky diodes. A Schottky diode (also known as Schottky barrier diode or hot-carrier diode) is a semiconductor diode formed by the junction of a semiconductor with a metal. It has a low forward voltage drop and a very fast switching action.

SELECT EXAMPLES

Example 1 provides an apparatus for a self-aligned light angle sensor which forgoes the need for calibration comprising a substrate, a cathode disposed on the substrate, an intrinsic layer disposed on the cathode.

In the first example, left and right channels are configured to comprise a left and right anode, each of which is disposed on the intrinsic layer and configured to sense light therein. The first example further comprises a passivation layer at least partially covering the left and right anode and a blocking member disposed proximally to the left and right anode.

Example 2 provides a self-aligned light angle sensor according to example 1 wherein the left and right anodes comprise metal.

Example 3 provides a self-aligned light angle sensor according to example 1 wherein the left and right anodes comprise a metal silicide.

Example 4 provides a self-aligned light angle sensor according to example 3 wherein the metal silicide is configured as a Schottky diode.

Example 5 provides a self-aligned light angle sensor according to example 1 wherein the blocking member comprises metal.

Example 6 provides a self-aligned light angle sensor according to example wherein the intrinsic layer comprises undoped silicon.

Example 7 provides a self-aligned light angle sensor according to example further comprising a dielectric layer disposed over blocking member.

Example 8 provides a self-aligned light angle sensor according to example 7 further comprising an optical filter.

Example 9 provides a self-aligned light angle sensor according to example 1 wherein substrate is configured to be the cathode.

Example 10 provides a method for fabricating a self-aligned light angle sensor, the method comprising: providing a substrate, depositing a cathode on the substrate, epitaxially growing an intrinsic layer on the cathode, providing a left and right anode, each of which is disposed on the intrinsic layer and configured to sense light therein.

In the tenth example, the method further provides depositing a passivation layer at least partially covering the left and right anode and disposing a blocking member proximally to the left and right anode.

Example 11 provides a method according to example 10 wherein the left and right anodes comprise a metal silicide.

Example 12 provides a method according to example 11 further comprising configuring the metal silicide to function as a Schottky diode.

Example 13 provides a method according to example 10 wherein the blocking member comprises a very thin layer of metal.

Example 14 provides a method according to example 10 wherein the intrinsic layer comprises undoped silicon.

Example 15 provides a method according to example 10 further comprising depositing an optical filter.

Example 16 provides a method according to example 10 further comprising measuring a first current on the left anode and a second current on the right anode.

Example 17 provides a method according to example 16 further comprising calculating a ratio of the first and second currents.

Example 18 provides a method according to example 17 further comprising deriving an angle of incidence based on the ratio of the first and second currents.

Example 19 provides an apparatus comprising a means for providing a substrate, a means for depositing a cathode on the substrate, a means for epitaxially growing an intrinsic layer on the cathode, a means for providing a left and right anode, each of which is disposed on the intrinsic layer and configured to sense light therein, a means for depositing a passivation layer at least partially covering the left and right anode, and a means for disposing a blocking member proximally to the left and right anode.

Example 20 provides for an apparatus according to example 19 further comprising an analog front end configured to derive an angle of incidence based on a ratio of the first and second currents measure from the left and right anodes, respectively.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein.

Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The foregoing outlines features of one or more embodiments of the subject matter disclosed herein. These embodiments are provided to enable a person having ordinary skill in the art (PHOSITA) to better understand various aspects of the present disclosure. Certain well-understood terms, as well as underlying technologies and/or standards may be referenced without being described in detail. It is anticipated that the PHOSITA will possess or have access to background knowledge or information in those technologies and standards sufficient to practice the teachings of the present disclosure.

The PHOSITA will appreciate that they may readily use the present disclosure as a basis for designing or modifying other processes, structures, or variations for carrying out the same purposes and/or achieving the same advantages of the embodiments introduced herein. The PHOSITA will also recognize that such equivalent constructions do not depart from the spirit and scope of the present disclosure, and that they may make various changes, substitutions, and alterations herein without departing from the spirit and scope of the present disclosure.

The above-described embodiments may be implemented in any of numerous ways. One or more aspects and embodiments of the present application involving the performance of processes or methods may utilize program instructions executable by a device (e.g., a computer, a processor, or other device) to perform, or control performance of, the processes or methods.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above.

The computer readable medium or media may be transportable, such that the program or programs stored thereon may be loaded onto one or more different computers or other processors to implement various ones of the aspects described above. In some embodiments, computer readable media may be non-transitory media.

Note that the activities discussed above with reference to the FIGURES which are applicable to any integrated circuit that involves signal processing (for example, gesture signal processing, video signal processing, audio signal processing, analog-to-digital conversion, digital-to-analog conversion), particularly those that can execute specialized software programs or algorithms, some of which may be associated with processing digitized real-time data.

In some cases, the teachings of the present disclosure may be encoded into one or more tangible, non-transitory computer-readable mediums having stored thereon executable instructions that, when executed, instruct a programmable device (such as a processor or DSP) to perform the methods or functions disclosed herein. In cases where the teachings herein are embodied at least partly in a hardware device (such as an ASIC, IP block, or SoC), a non-transitory medium could include a hardware device hardware-programmed with logic to perform the methods or functions disclosed herein. The teachings could also be practiced in the form of Register Transfer Level (RTL) or other hardware description language such as VHDL or Verilog, which can be used to program a fabrication process to produce the hardware elements disclosed.

In example implementations, at least some portions of the processing activities outlined herein may also be implemented in software. In some embodiments, one or more of these features may be implemented in hardware provided external to the elements of the disclosed figures, or consolidated in any appropriate manner to achieve the intended functionality. The various components may include software (or reciprocating software) that can coordinate in order to achieve the operations as outlined herein. In still other embodiments, these elements may include any suitable algorithms, hardware, software, components, modules, interfaces, or objects that facilitate the operations thereof.

Any suitably-configured processor component can execute any type of instructions associated with the data to achieve the operations detailed herein. Any processor disclosed herein could transform an element or an article (for example, data) from one state or thing to another state or thing. In another example, some activities outlined herein may be implemented with fixed logic or programmable logic (for example, software and/or computer instructions executed by a processor) and the elements identified herein could be some type of a programmable processor, programmable digital logic (for example, an FPGA, an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof.

In operation, processors may store information in any suitable type of non-transitory storage medium (for example, random access memory (RAM), read only memory (ROM), FPGA, EPROM, electrically erasable programmable ROM (EEPROM), etc.), software, hardware, or in any other suitable component, device, element, or object where appropriate and based on particular needs. Further, the information being tracked, sent, received, or stored in a processor could be provided in any database, register, table, cache, queue, control list, or storage structure, based on particular needs and implementations, all of which could be referenced in any suitable timeframe.

Any of the memory items discussed herein should be construed as being encompassed within the broad term 'memory.' Similarly, any of the potential processing elements, modules, and machines described herein should be construed as being encompassed within the broad term 'microprocessor' or 'processor.' Furthermore, in various embodiments, the processors, memories, network cards, buses, storage devices, related peripherals, and other hardware elements described herein may be realized by a processor, memory, and other related devices configured by software or firmware to emulate or virtualize the functions of those hardware elements.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a personal digital assistant (PDA), a smart phone, a mobile phone, an iPad, or any other suitable portable or fixed electronic device.

Also, a computer may have one or more input and output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Computer-executable instructions may be in many forms, such as program modules, executed by one or more computers or other devices. Generally, program modules include routines, programs, objects, components, data structures, etc. that performs particular tasks or implement particular abstract data types. Typically, the functionality of the program modules may be combined or distributed as desired in various embodiments.

The terms "program" or "software" are used herein in a generic sense to refer to any type of computer code or set of computer-executable instructions that may be employed to program a computer or other processor to implement various aspects as described above. Additionally, it should be appreciated that according to one aspect, one or more computer programs that when executed perform methods of the present application need not reside on a single computer or processor, but may be distributed in a modular fashion among a number of different computers or processors to implement various aspects of the present application.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code may be executed on any suitable processor or collection of processors, whether provided in a single computer or distributed among multiple computers.

Computer program logic implementing all or part of the functionality described herein is embodied in various forms, including, but in no way limited to, a source code form, a computer executable form, a hardware description form, and various intermediate forms (for example, mask works, or forms generated by an assembler, compiler, linker, or locator). In an example, source code includes a series of computer program instructions implemented in various programming languages, such as an object code, an assembly language, or a high-level language such as OpenCL, RTL, Verilog, VHDL, Fortran, C, C++, JAVA, or HTML for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

In some embodiments, any number of electrical circuits of the FIGURES may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), memory elements, etc. can be suitably coupled to the board based on particular configuration needs, processing demands, computer designs, etc.

Other components such as external storage, additional sensors, controllers for audio/video display, and peripheral devices may be attached to the board as plug-in cards, via cables, or integrated into the board itself. In another example embodiment, the electrical circuits of the FIGURES may be implemented as standalone modules (e.g., a device with associated components and circuitry configured to perform a specific application or function) or implemented as plug-in modules into application-specific hardware of electronic devices.

Note that with the numerous examples provided herein, interaction may be described in terms of two, three, four, or more electrical components. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this disclosure.

In certain cases, it may be easier to describe one or more of the functionalities of a given set of flows by only referencing a limited number of electrical elements. It should be appreciated that the electrical circuits of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Interpretation of Terms

All definitions, as defined and used herein, should be understood to control over dictionary definitions, definitions in documents incorporated by reference, and/or ordinary meanings of the defined terms. Unless the context clearly requires otherwise, throughout the description and the "comprise," "comprising," and the like are to be construed in an inclusive sense, as opposed to an exclusive or exhaustive sense; that is to say, in the sense of "including, but not limited to".

"connected," "coupled," or any variant thereof, means any connection or coupling, either direct or indirect, between two or more elements; the coupling or connection between the elements can be physical, logical, or a combination thereof.

"herein," "above," "below," and words of similar import, when used to describe this specification shall refer to this specification as a whole and not to any particular portions of this specification.

"or," in reference to a list of two or more items, covers all of the following interpretations of the word: any of the items in the list, all of the items in the list, and any combination of the items in the list.

the singular forms "a", "an" and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined.

Elements other than those specifically identified by the "and/or" clause may optionally be present, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "between" is to be inclusive unless indicated otherwise. For example, "between A and B" includes A and B unless indicated otherwise.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke 35 U.S.C. § 112(f) as it exists on the date of the filing hereof unless the words "means for" or "steps for" are specifically used in the particular claims; and (b) does not intend, by any statement in the disclosure, to limit this disclosure in any way that is not otherwise reflected in the appended claims.

The present invention should therefore not be considered limited to the particular embodiments described above. Various modifications, equivalent processes, as well as numerous structures to which the present invention may be applicable, will be readily apparent to those skilled in the art to which the present invention is directed upon review of the present disclosure.

What is claimed is:

1. A self-aligned light angle sensor which forgoes the need for calibration comprising:
    a substrate;
    a cathode disposed on the substrate;
    an intrinsic layer disposed on the cathode;
    left and right anodes, each of which is disposed on the intrinsic layer and configured to sense light therein, wherein the left and right anodes comprise a metal;
    a blocking member disposed proximally to the left and right anodes; and
    a passivation layer between the blocking member and each of the left and right anodes.

2. The self-aligned light angle sensor according to claim 1 wherein the left and right anodes comprise a metal silicide.

3. The self-aligned light angle sensor according to claim 2 wherein the metal silicide is configured as a Schottky diode.

4. The self-aligned light angle sensor according to claim 1 wherein the blocking member comprises metal.

5. The self-aligned light angle sensor according to claim 1 wherein the intrinsic layer comprises undoped silicon.

6. The self-aligned light angle sensor according to claim 1 further comprising a dielectric layer disposed over blocking member.

7. The self-aligned light angle sensor according to claim 6 further comprising an optical filter.

8. The self-aligned light angle sensor according to claim 1 wherein substrate is configured to be the cathode.

9. A light angle sensor comprising:
    a cathode;
    an intrinsic layer disposed on the cathode;
    left and right anodes, each of which is disposed on the intrinsic layer and configured to sense light therein;
    a blocking member disposed proximally to the left and right anodes; and
    a passivation layer between the blocking member and each of the left and right anodes,
    wherein the left and right anodes comprise a metal silicide.

10. The light angle sensor according to claim 9 further comprising configuring the metal silicide to function as a Schottky diode.

11. The light angle sensor according to claim 9, wherein the passivation layer is configured to prevent short circuiting through the blocking member.

12. The light angle sensor according to claim 9, wherein the blocking member is configured to block light between the left and right anodes.

13. A light angle sensor comprising:
    a cathode;
    an intrinsic layer disposed on the cathode;
    left and right anodes, each of which is disposed on the intrinsic layer and configured to sense light therein, wherein the left and right anodes comprise a metal silicide;
    a first blocking member disposed proximally to the left anode;
    a second blocking member disposed proximally to the right anode, the second blocking member spaced apart from the first blocking member; and
    a passivation layer between the first blocking member and the left anode and between the second blocking member and the right anode.

14. The light angle sensor according to claim 13, wherein the passivation layer is configured to prevent short circuiting through the first block member.

15. The light angle sensor according to claim 13, wherein the passivation layer is configured to prevent short circuiting through the second block member.

16. The light angle sensor according to claim 13, wherein the first and second blocking members comprise metal.

* * * * *